US009968732B2

(12) United States Patent
Drew et al.

(10) Patent No.: US 9,968,732 B2
(45) Date of Patent: May 15, 2018

(54) INTERFACE FOR IMPLANTABLE MEDICAL DEVICE PROGRAMMING

(75) Inventors: Touby A. Drew, Golden Valley, MN (US); Steven M. Goetz, North Oaks, MN (US); Sarah B. Alme, Blaine, MN (US); Jiaying Shen, Maple Grove, MN (US); Ajinkya M. Joglekar, Maple Grove, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 1620 days.

(21) Appl. No.: 12/502,321

(22) Filed: Jul. 14, 2009

(65) Prior Publication Data

US 2010/0010646 A1 Jan. 14, 2010

Related U.S. Application Data

(60) Provisional application No. 61/080,427, filed on Jul. 14, 2008.

(51) Int. Cl.

| | |
|---|---|
| ***A61M 5/142*** | (2006.01) |
| ***A61N 1/372*** | (2006.01) |
| ***G06F 19/00*** | (2018.01) |
| *A61N 1/36* | (2006.01) |

(52) U.S. Cl.

CPC ..... *A61M 5/14276* (2013.01); *A61N 1/37247* (2013.01); *G06F 19/3468* (2013.01); *A61M 2205/505* (2013.01); *A61N 1/3605* (2013.01); *G16H 15/00* (2018.01)

(58) Field of Classification Search

USPC .................................. 345/156–173; 715/600

See application file for complete search history.

(56) References Cited

U.S. PATENT DOCUMENTS

| | | | | |
|---|---|---|---|---|
| 4,692,147 | A | 9/1987 | Duggan | |
| 5,370,672 | A * | 12/1994 | Fowler et al. | 607/58 |
| 5,782,798 | A | 7/1998 | Rise | |
| 5,814,014 | A | 9/1998 | Elsberry et al. | |
| 6,595,430 | B1 * | 7/2003 | Shah | 236/46 R |

(Continued)

FOREIGN PATENT DOCUMENTS

WO 2002058619 A 8/2002

OTHER PUBLICATIONS

International Search Report dated Sep. 17, 2009, in co-pending PCT application, PCT/US2009/050457.

(Continued)

*Primary Examiner* — Grant Sitta

(74) *Attorney, Agent, or Firm* — Beth I. McMahon; Medtronic, Inc.

(57) ABSTRACT

An implantable medical device is capable of delivering therapeutic output to a patient. A controller, programmable by a medical professional, is operatively coupled to the implantable medical device to, in part, program the therapeutic output to be delivered to the patient. The controller has an interface allowing the medical professional to graphically select an amount of the therapeutic output to be delivered to the patient in at least one of a series of discrete timer intervals. The graphic selection may be aided by the use of a light pen or other pointing device to sketch the infusion pattern. Computer programs using algorithms may be utilized to translate the information inputted through the light pen into an infusion program.

32 Claims, 33 Drawing Sheets

(56) References Cited

U.S. PATENT DOCUMENTS

| | | | | |
|---|---|---|---|---|
| 2004/0111131 | A1* | 6/2004 | Hu et al. | 607/60 |
| 2004/0225252 | A1* | 11/2004 | Gillespie et al. | 604/19 |
| 2006/0041222 | A1* | 2/2006 | Dewing et al. | 604/93.01 |
| 2007/0203643 | A1 | 8/2007 | Stone et al. | |
| 2008/0231635 | A1* | 9/2008 | Saund | 345/440 |
| 2009/0212966 | A1* | 8/2009 | Panduro | 340/825.22 |

OTHER PUBLICATIONS

Medtronic Brochure, "RestoreUltra", 2008, Brochure Publication No. UC200801088a.

* cited by examiner

PATIENT RECORD
Patient List
Session List
Nom de famille: Doe
Prénom: John
Patient Id: 990011
Fecha de nacimiento: 5/16/1985
Sexe: Femmin
Patient Status: Inactive
Personal
Device
Sessions
TabItem
Address:
City:
State:
ZIP Code:
County:
Home Phone:
Autre téléphone:
Physician:
Note:
Reports
Save Changes
Delete Patient Navigation A: Vertical Side Bar Navigation B: Horizontal Top Bar

INTERFACE FOR IMPLANTABLE MEDICAL DEVICE PROGRAMMING

RELATED APPLICATION

This application claims the benefit of the filing date of a provisional U.S. Application Ser. No. 61/080,427, filed Jul. 14, 2008.

FIELD

This invention relates generally to a programmer for an implantable medical device. More particularly, the present invention relates to a computer method and apparatus for programming parameters into an implantable medical device.

BACKGROUND

Implantable medical devices for producing a therapeutic result in a patient are well known. Examples of such implantable medical devices include implantable drug infusion pumps, implantable neurostimulators, implantable cardioverters, implantable cardiac pacemakers, implantable defibrillators, cochlear implants, and others that now exist or may exist in the future. These devices are intended to provide a patient with a therapeutic output to alleviate or assist with a variety of conditions. Typically such devices are implanted in a patient and provide a therapeutic output under specified conditions on a recurring basis.

One type of implantable medical device is a drug infusion device which can deliver a medication, typically fluid medication, to a patient at a selected site. A drug infusion device may be implanted at a location in the body of a patient and deliver a fluid medication through a catheter to a selected delivery site in the body. Examples of such devices are described in U.S. Pat. No. 5,782,798 to Rise, entitled Techniques For Treating Eating Disorders By Brain Stimulation and Drug Infusion; U.S. Pat. No. 5,814,014 to Elsberry et al., entitled Techniques of Treating Neurodegenerative Disorders by Brain Infusion, each assigned to Medtronic, Inc., Minneapolis, Minn.

Another type of implantable medical device is an electrical stimulation device. An electrical nerve stimulator can also be implanted in the body of a patient and can stimulate selected nerves in the body in accordance with a specified routine. The electrical nerve stimulator may be implanted at a location in the body and deliver electrical stimulation pulses through a lead or leads to a stimulus site. One example of such an implantable electrical stimulation device is Medtronic's RestoreUltra™ neurostimulator.

It is desirable to be able to non-invasively program an implanted medical device, such as a drug infusion device or an electrical stimulation device, in order to change the therapeutic regimen without incurring unnecessary trauma to the patient. An example of such a device is described in U.S. Pat. No. 4,692,147 to Duggan, entitled Drug Administration Device, assigned to Medtronic, Inc., which can be non-invasively programmed to change both the dosage amount and the dosage interval. Verification of the received dosage and interval commands are achieved by means of an audio transducer which is attached to the device case. The implantable drug administration device described in Duggan allows a medical professional to program the delivery rate of a drug contained in the reservoir of the device over a specified interval. The process, however, may be labor intensive.

Non-invasively programmable implantable medical devices are typically programmed using an external programming device, sometimes known as a controller, which can communicate with the implanted medical device through well known techniques such as telemetry. An external controller, or programmer, can be used by a medical professional, for example, to change the therapeutic regimen by increasing or decreasing the amount of fluid medication delivered or by increasing or decreasing the intensity or timing or characteristic of an electrical stimulation signal. Typically, a medical professional interfaces with the external controller or programmer to set various parameters associated with the implantable medical device and then transmits, or downloads, those parameters to the implanted medical device. The external device may also record other information important to the delivery of the therapeutic output although not actually downloaded to the implanted medical, e.g., patient information, implanted device information such as model, volume, implant location, length of catheter or lead, and other information specific to different devices.

BRIEF SUMMARY OF THE INVENTION

A programmer for an implantable medical device capable of delivery therapeutic output to a patient comprising an interface through which a user may graphically sketch an infusion program using a graphical user interface device, the sketched infusion program including at least one dosage amount scheduled to run over a time duration, both the dosage amount and the time duration created by the shape and location of the sketch, and a computer operably connected to the interface to interpret the sketch.

In another embodiment, the present invention may include a method of creating an infusion program using a controller including presenting an interface that includes a graphical drawing tablet, wherein the graphical drawing tablet includes one axis for time and one axis for dosage rate, inputting a dosage pattern using a graphical user interface device, and editing the dosage pattern if desired.

Included herein is a method for programming a therapy delivery schedule comprising providing a programmer with a graphical user interface, drawing with a pointing device on the graphical user interface one or more figures representing the desired therapy schedule, and translating the figures into a therapy delivery schedule.

Another embodiment may include a programmer for an implantable medical device capable of delivery therapeutic output to a patient that includes an interface through which a user may graphically sketch one or more portions of an infusion program using a pointing device, the sketched infusion program including at least one dosage amount scheduled to run over a desired time duration, both the dosage amount and the time duration created by the shape and location of the sketch, a computer operably connected to the interface to interpret the sketch.

Another aspect of the present invention may include a method of creating an infusion program using a controller including presenting an interface that includes a graphical drawing tablet, wherein the graphical drawing tablet includes one axis for time and one axis for dosage rate, inputting a pattern using a pointing device to indicate the desired dosage and time, and editing the pattern.

Also part of the present invention is a method for editing a therapy delivery schedule that includes providing a programmer with a graphical user interface, displaying on the graphical user interface one or more figures representing the desired therapy schedule, each figure representing a therapy dosage, selecting one or more of the figures representing one or more dosages, editing with a pointing device the selected figures whereby expanding or contracting the figures along a first axis increases or decreases the duration of the dosage and expanding or contracting the figures along a second axis increases or decreases the rate of delivery of the dosage.

Yet another embodiment may include a programmer for an implantable medical device capable of delivery therapeutic output to a patient comprising an interface through which one or more portions of an infusion program are graphically displayed as one or more figures, each figure graphically representing the dosage rate and the dosage duration by the size and shape of the figure, and a pointing device for selecting one or more figures whereby expanding or contracting the figures along a first axis increases or decreases the duration of the dosage and expanding or contracting the figures along a second axis increases or decreases the rate of delivery of the dosage.

BRIEF DESCRIPTION OF THE DRAWINGS

Embodiments of the present invention will hereinafter be described in conjunction with the following drawings wherein like reference numerals denote like elements throughout.

DETAILED DESCRIPTION OF THE INVENTION

The present invention relates to an external programmer 20 which is utilized to interface with an implantable medical device 14 implanted into a patient 10. The programmer 20 may display information and receive instructions through a user interface that incorporates a standard computing platform such as a personal computer. Other computing platforms may include a virtual environment, internet infrastructure, personal digital assistants, and others. In one embodiment, the external programmer 20 may be used by a medical professional to gather information from the implantable device 14 and also to program or otherwise download information to the implantable device 14. The medical professional may be a doctor, clinician, nurse, or other patient caregiver who is responsible for procedures relating to the implantable medical device 14, such as updating the programming, refilling, changing the dosing, or other tasks associated with an implantable device 14. The person using the programmer 20 to extract or input information to the implantable device 14 will be referred to herein as a "user." The programmer 20 may also be known as a controller, a programmer, or by other names known to those of skill in the art.

Figure 1:
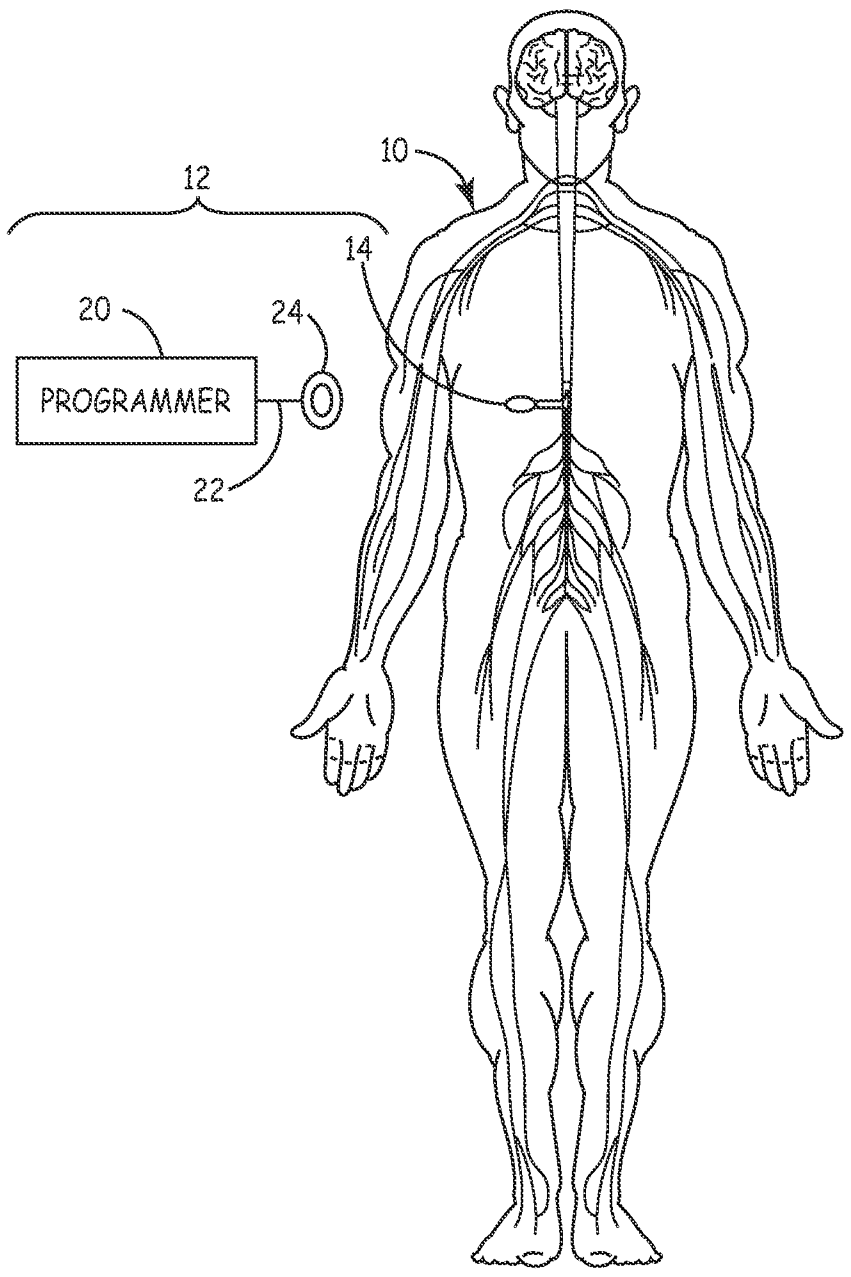
FIG. 1 is a schematic view of an implantable device implanted in a person and a controller.

In one embodiment the programmer 20 may include a remote device 24 placed near to the patient for communication purposes. The remote device 24 may be connected to the programmer 20 through a cord or through a wireless communication protocol. The remote device 24 may in turn communicate with the implantable device 14. The programmer 20, remote device 24, and connector 22 may be collectively referred to as system 12. FIG. 1 is therefore a schematic view of a drug infusion system 12 with implantable drug infusion device 14 implanted within the body of patient 10. Methods of communicating with implanted treatment devices using radio frequency telemetry, inductive communication, and other formats in order to program such implanted drug infusion devices are well known in the art. The programmer 20 may be a dedicated handheld device or workstation or, in other embodiments, the programmer 20 may be a standard personal computer or other device that can operate an interface as described herein. The screens and operating system that are run on the programmer 20 may be the same or similar for both.

With regard to references in this specification to computers, the computer, if included, may be any standard computer including standard attachments and components thereof (e.g., CD drives, etc.). The computer may include a mouse and keyboard and may include touch screen or other interfaces as known to those in the art. When various options on the following described pages are selected by the user, the user may use any compatible input device. The following description will reference the programmer 20 connected to remote device 24 though it should be understood that the programmer 20 may include a computer workstation and a remote device 24 connected thereto. However, this description will generally describe the programmer 20 as a stand alone hand held device.

In the present description the system 12 may be capable of delivering a therapeutic output to a patient 10 through the implantable medical device 14 and to specify the therapeutic output to be delivered. In other embodiments, the implantable medical device may instead be a sensor, recorder, analyzer, monitor or other medical device that does not provide therapy. The programmer 20 allows the medical professional to interface with the implanted medical device 14. Implantable device 14 can be any of a number of medical devices such as an implantable therapeutic substance delivery device, implantable drug pump, implantable electrical stimulator, cardiac pacemaker, cardioverter or defibrillator, for example. For purposes of illustration, the present invention will be described with respect to an implantable drug infusion device. However, it should be recognized and understood that the present invention has applicability to other types of implantable medical devices, e.g., implantable electrical stimulators.

FIG. 1 is a schematic view of a drug infusion system 12 with implantable drug infusion device 14 implanted within the body of patient 10. Drug infusion device 14 may be programmable through a telemetry link from programmer 20, which may be coupled via a conductor 22 to a radio frequency antenna 24. Drug infusion device 14 could be, but is not limited to being, a pump for infusing fluid medication into a patient's body.

Figure 2:
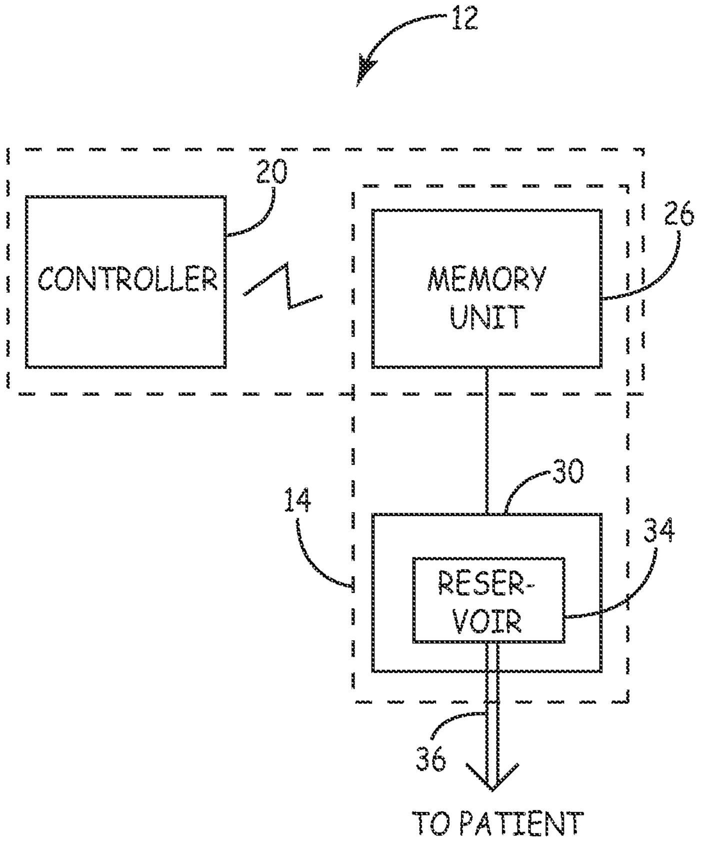
FIG. 2 is a block diagram of the system of FIG. 1.

FIG. 2 is a block diagram of drug infusion system 12 having an implantable drug infusion device 14. Drug infusion device 14 may include an internal memory unit 26 containing memory and programming that may provide instructions to drug delivery module 30. External programmer 20 may act as an input-output device for drug infusion device 14 and also provide computational support for memory unit 26. In general, drug delivery module 30 is a pump for infusing a fluid medication, including a drug or a combination of drugs, to patient 10. Drug delivery module 30 has a reservoir 34 for holding the fluid medication to be infused and is coupled to patient 10 through catheter tubing 36. Such drug delivery modules 30 are well known in the art. As may be appreciated, the drug infusion device 14 may include other components, such as a battery, remote charging equipment, etc., that are not shown here.

Figure 3:
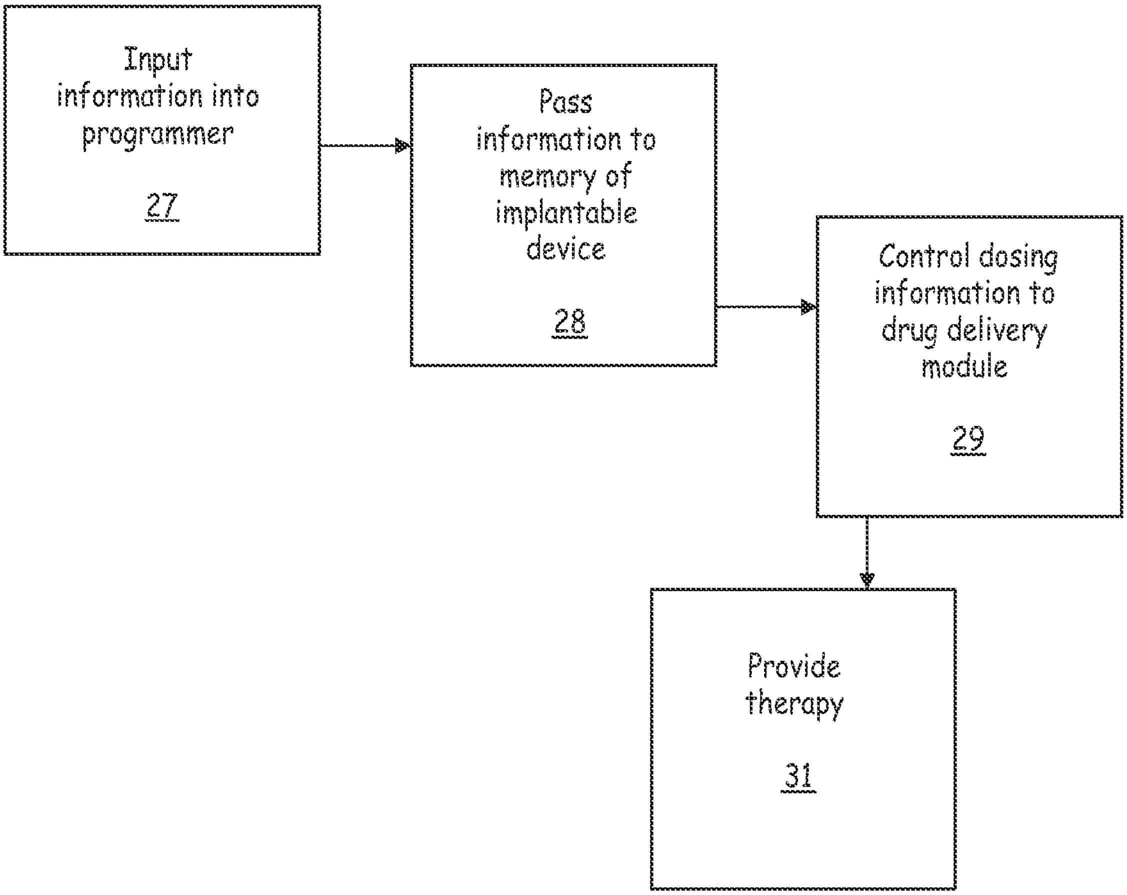
FIG. 3 is a block diagram illustrating the steps in programming an implantable medical device.

FIG. 3 may illustrate one example of a method of programming an implantable device 14 using a programmer. The user may input information into the programmer in step 27. The programmer may pass the information through the remote device 24 to the memory 26 of the implantable device 14 in step 28. Programming information, once stored in memory unit 26, will then provide the dosing regimen to be performed by drug delivery module 30 in step 29. As may be appreciated, a variety of terminology may be utilized when referring to the dosing pattern and the specific dosages in the pattern. Dose, dosages, rate, dosage rate, step and other terms may be used interchangeably to describe the therapy being programmed and delivered. In this description the term 'rate' will generally describe how fast the therapy material is pumped by the implantable device into the patient. The terms duration or time will generally be utilized to describe the length of time over which the therapy is delivered at the selected rate.

A programmer 20 that may be capable of interacting with drug infusion devices are well known in the art. Similarly, techniques for non-invasively communicating between controllers 20 and implanted drug infusion devices, such as by telemetry, are also well known.

Programmer 20 may require certain inputs of data or information from the user in order to adequately and fully control an implanted medical device 14. The types of information input can range from patient information, e.g., to keep track of programming regimens among various patients, implantable medical device type and model, and perhaps serial number, capacity or reservoir size, catheter volume, implantation date and implantation location and/or orientation, as well as information related to the programmability functions of the implanted medical device. If the implanted medical device 14 is a drug infusion device, information may need to be input or obtained regarding fluid medication prescription, kinds and amounts or concentrations of fluid medications, amount of fluid medication filled into the reservoir, the infusion program, including constant or variable dosage, daily changes, and patient administered options such as boluses. Further, information may also need to be obtained regarding a special initial infusion, commonly referred to as a prime bolus or a purge, to account for the initial volume of fluid contained in the catheter 36, which may or may not be the same as the fluid medication contained in the reservoir 34. Still further, upon refilling the implanted drug infusion device 14 with a new supply of fluid medication, information may be needed regarding a special interim infusion, commonly referred to as a bridge bolus, to account for any change in kind or concentration of fluid medication. Alarms may need to be programmed or set or silenced regarding various anomalies that may occur during programming or infusion. And still further, information may need to be supplied or displayed regarding refill procedures, such as the estimated time to refill or estimated time to battery replacement or explantation. These types of items are generally referred to as tasks throughout this description. As can be seen, there may be a number of variables involving a not insignificant amount of information.

Various procedures may need to be undertaken by a user using the programmer 20. As an example, the user may know that the drug infusion device has been newly implanted into the patient 10 and needs to be set up and initially programmed. As another example, the user may know that the drug infusion device has just been refilled with a different fluid medication, kind or concentration, and needs to be re-programmed. It can be recognized that each of these medical procedures may require a different sets of tasks to be performed in order to accomplish the particular procedure involved. For example, an initial implantation procedure may require data to be input regarding the patient's name and particulars. However, during a refill procedure, information regarding the patient may not need to be reviewed or modified unless a change has occurred, as by a name change associated with marriage, for example. As another example, an initial implantation procedure typically will require the use of a prime bolus but not a bridge bolus. Conversely, a refill procedure may require the use of a bridge bolus but not a prime bolus. Therefore, different procedures may require different tasks wherein having an initial menu to select the correct group of tasks would be advantageous.

Figure 4:
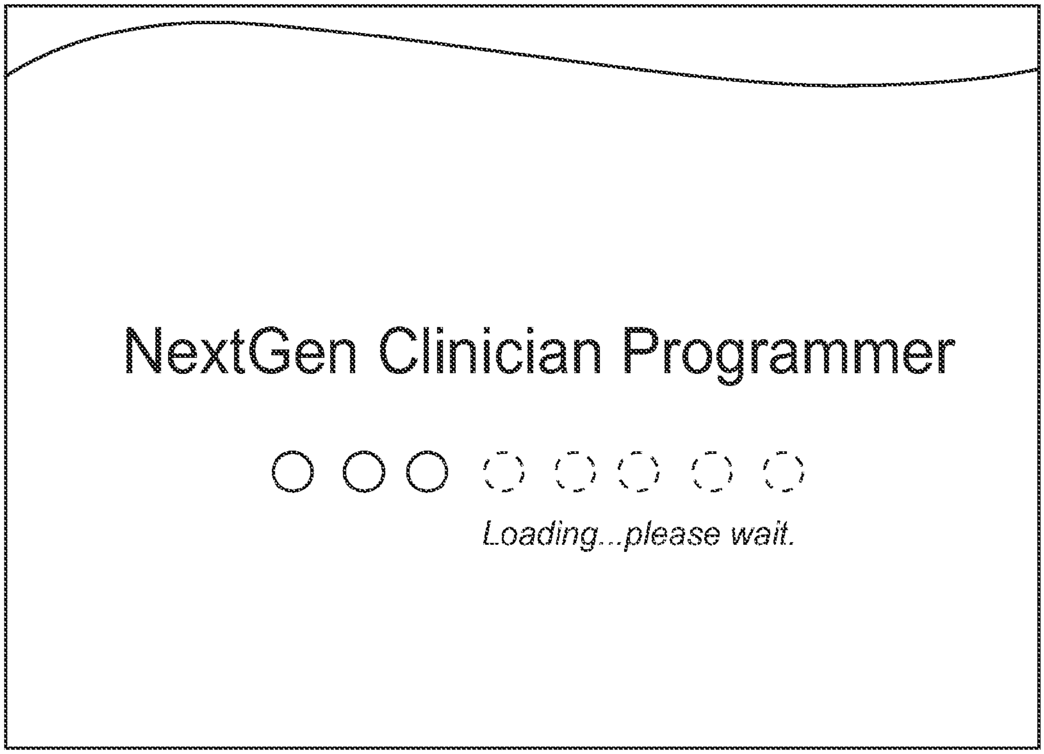
FIG. 4 illustrates a screen shot of a loading screen.
Figure 5:
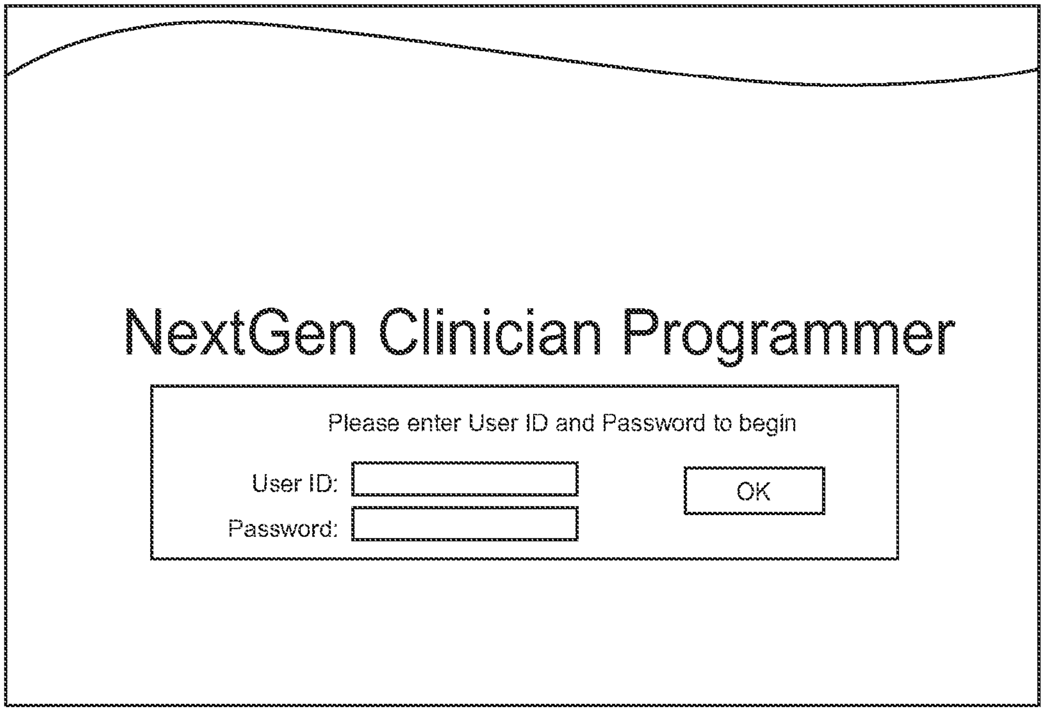
FIG. 5 illustrates a screen shot of a user log-in screen.
Figure 6:
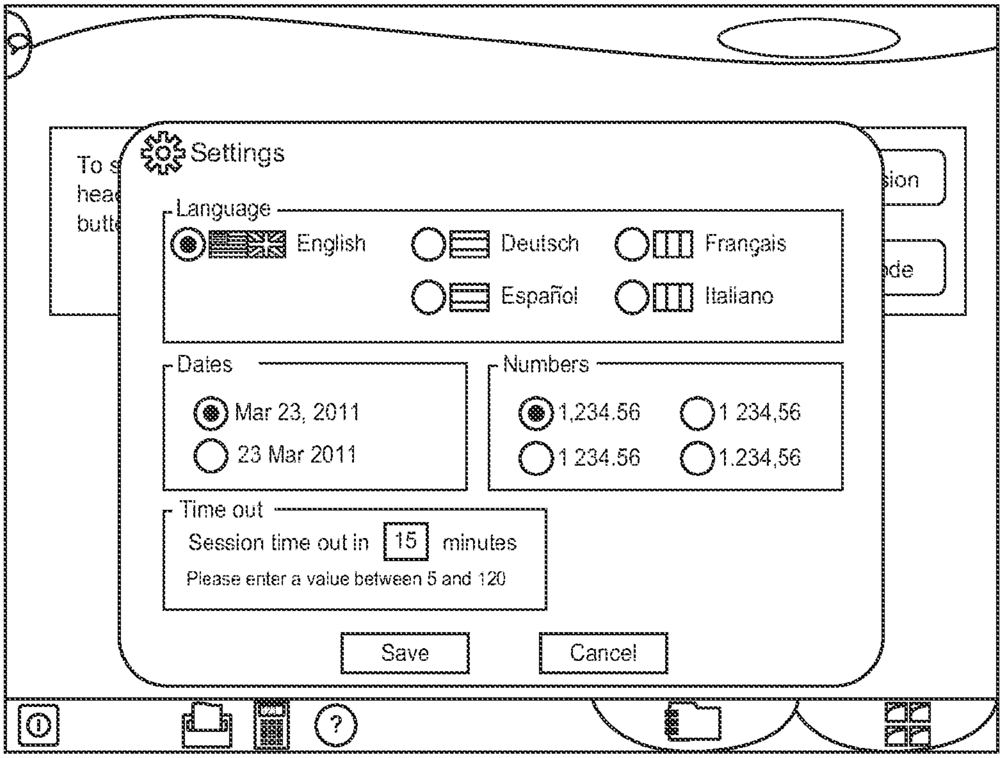
FIG. 6 illustrates a screen shot of a user settings screen.
Figure 7A:
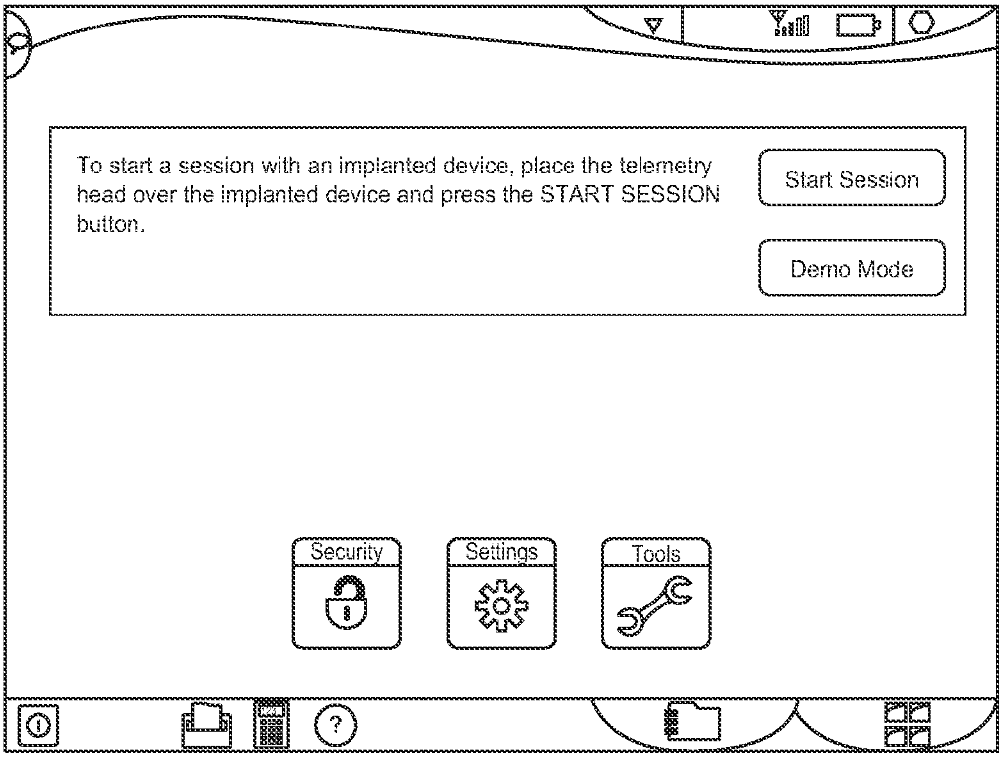
FIG. 7A illustrates a screen shot of a menu for starting to work with the programmer.
Figure 7B:
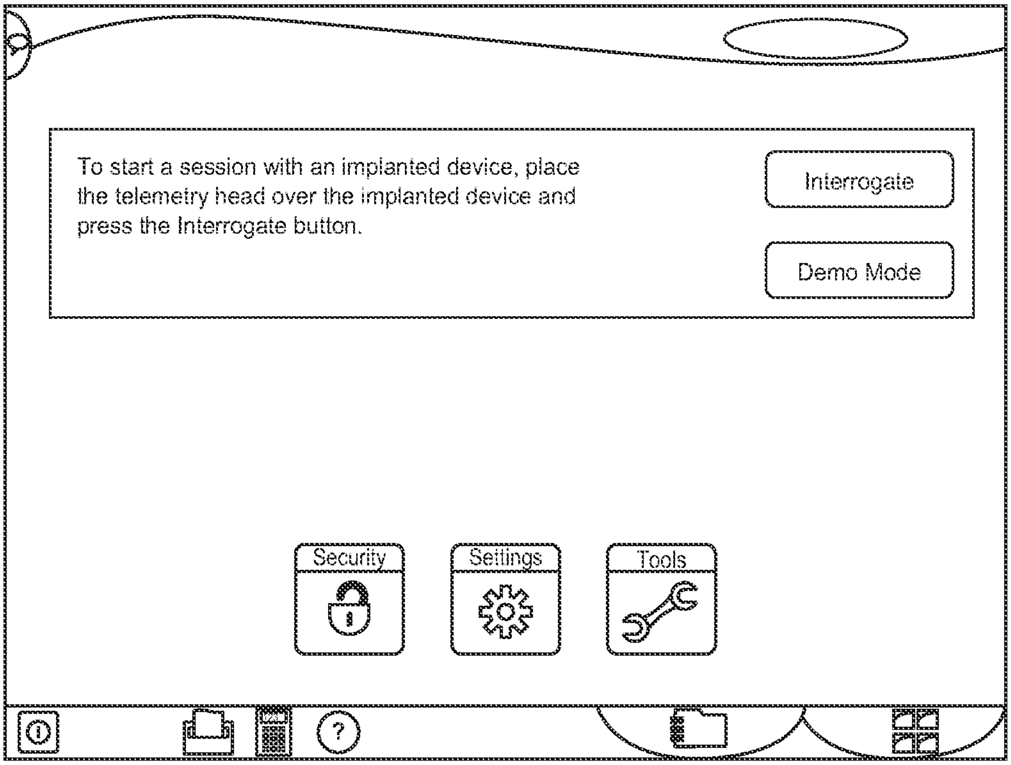
FIG. 7B illustrates another screen shot of a menu for starting to work with the programmer.
Figure 9:
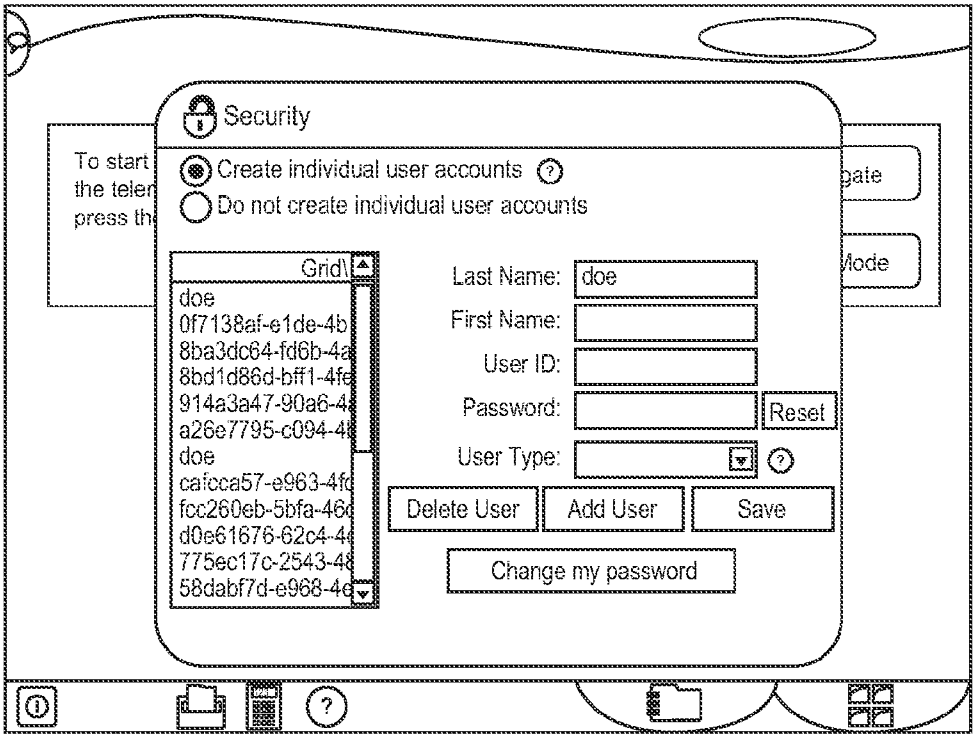
FIG. 9 illustrates a administration in screen.

FIG. 4 illustrates an example initial start up screen for one embodiment of the programmer 20. As previously stated, the programmer 20 can be accessed and controlled directly using a handheld device, a dedicated work station, or a personal computer with the appropriate software loaded thereon, each of which may include a connection to remote device 24 that sends and receives signals to the implantable device 14. Such a screen will provide notice to the user that the program is beginning operation. As illustrated in FIG. 5, a page for logging into the system using an identification and password may also be utilized. When the user logs into the system 12 for the first time the system 12 may query the user regarding certain user preferences as illustrated in FIG. 6. Such preferences may include language, the date, and other related preferences. Once this information is entered, and in subsequent sessions, the system 12 may instead first present the user with a list of system options, such as illustrated in FIG. 7A. The user may start a programming session by selecting "Start Session" on the programmer 20. FIG. 7B illustrates another screen shot for starting a session wherein the option includes the ability to "Interrogate" the implanted device 14 to start the session. The user may select to begin a session by interrogating an implanted device 14 or may instead modify various security or other features. In other embodiments the user may utilize the programmer 20 to create infusion programs when not in contact with a patient. Such situations may include a demonstration mode. An example page for modifying a user's security features is illustrated in FIG. 9 and may include standard user information, such as name, user ID, password, etc. The settings screen illustrated in FIG. 6 may also be accessed from the option screen illustrated in FIG. 7. As may be appreciated, various other types of screens may be presented in FIG. 7 for selection by the user, including clicking on the tools icon to access programmer specific functionality. In still further embodiments, other search tools may be utilized for selecting patients, such as searching by drug, delivery rates, dosage ranges, or other defined criteria.

If the user selects the Interrogate icon, various screens (not shown) may instruct the user on the correct steps for interrogating the implanted device 14 using the programmer 20 and the remote device 24. As may be appreciated, various ways of establishing communication between the implanted device 14 and the programmer 20 may be utilized. These steps may be more fully put forth in co-pending U.S. application Ser. No. 11/206,654, filed on Aug. 18, 2005, the entirety of which is hereby incorporated by reference.

Furthermore, other screens (not shown) may be utilized to give summary information about the name of the patient, information concerning the date of last change of the programming of the implantable device 14, the last refill date, the quantity of the reservoir fill, the type of infusion, and the infusion program. Further, such screens may provide information concerning the drugs contained in the reservoir of the implantable device 14 and the amount of the daily dose of each drug. Dose details, pump and catheter information and information concerning the implantable device 14 itself may be obtained by selecting various icons on such screen(s).

Detailed pump information may be provided including model and serial number, implant location, implant orientation, catheter information and notes for future reference. In some cases, at least part of this information will already be known, having been obtained directly from the implanted medical device, e.g., pump model, serial number, reservoir size, calibration constant and ERI. Information concerning the length of the catheter may be inputted by making the selection and/or by tapping the numbers provided in the screen. Further information about the catheter, necessary for proper implementation of prime and bridge boluses, may be provided (further discussed below). Screens not shown may also provide information concerning the amount of drug contained in the reservoir of implantable drug infusion device 14.

Figure 8:
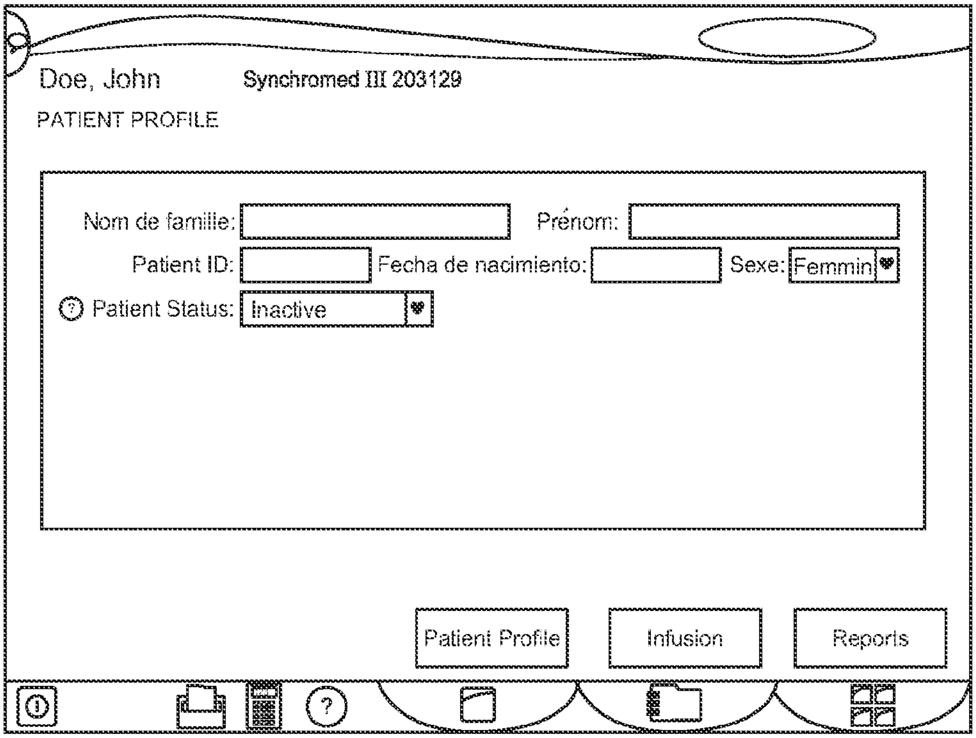
FIG. 8 illustrates a screen shot for finding a patient profile saved on the programmer.
Figure 10A:
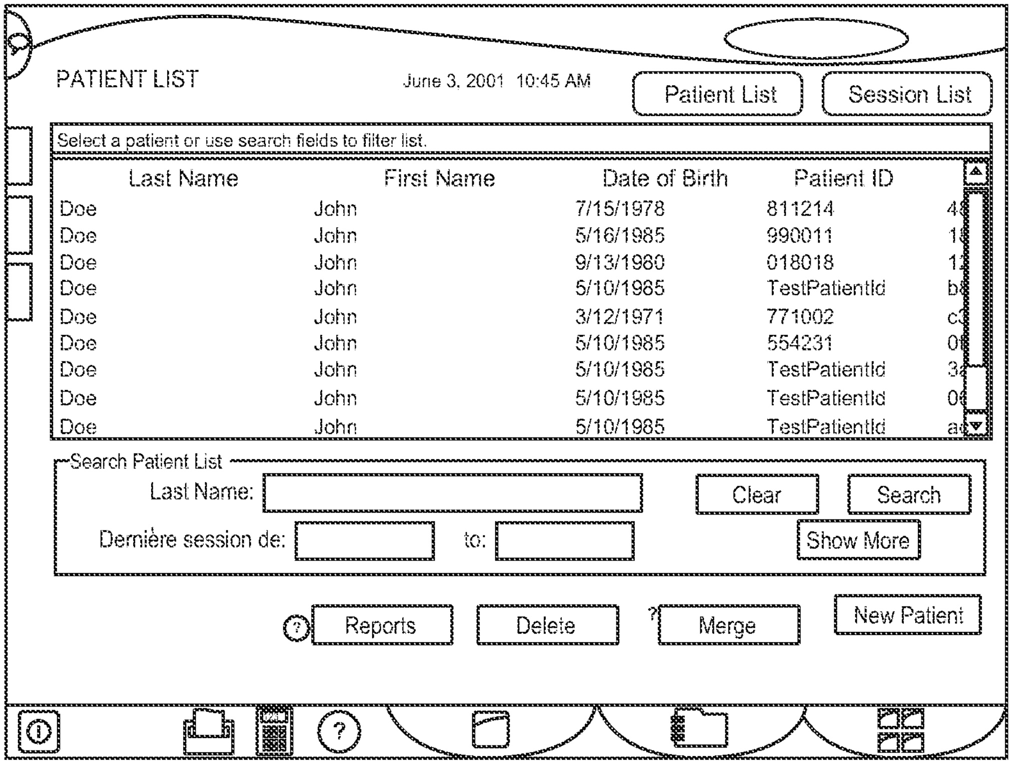
FIG. 10A illustrates a screen shot screen for finding a patient's saved information.
Figure 10B:
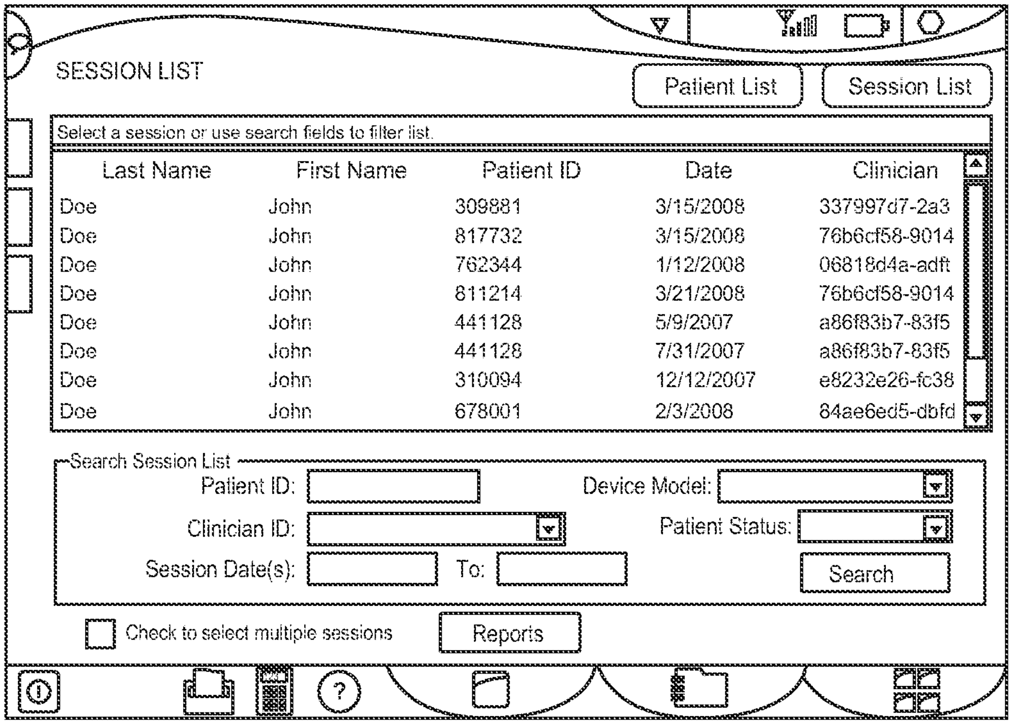
FIG. 10B illustrates another screen shot screen for finding a patient's saved information with different search term options.
Figure 11A:
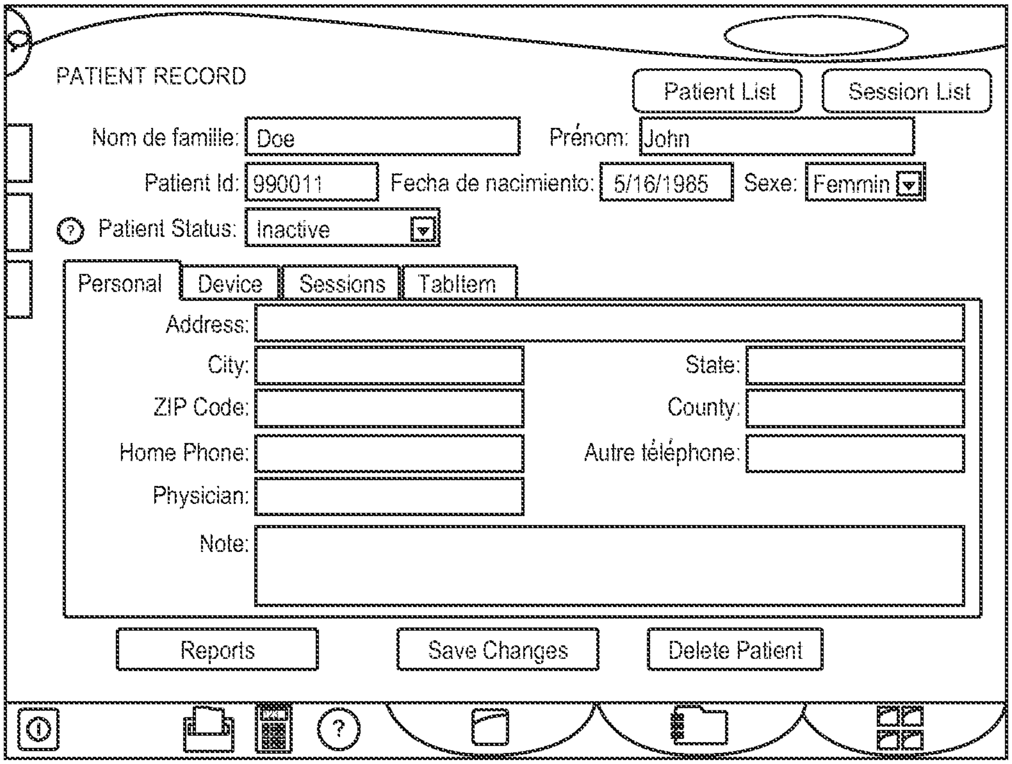
FIG. 11A illustrates a screen shot for displaying patient information.
Figure 11B:
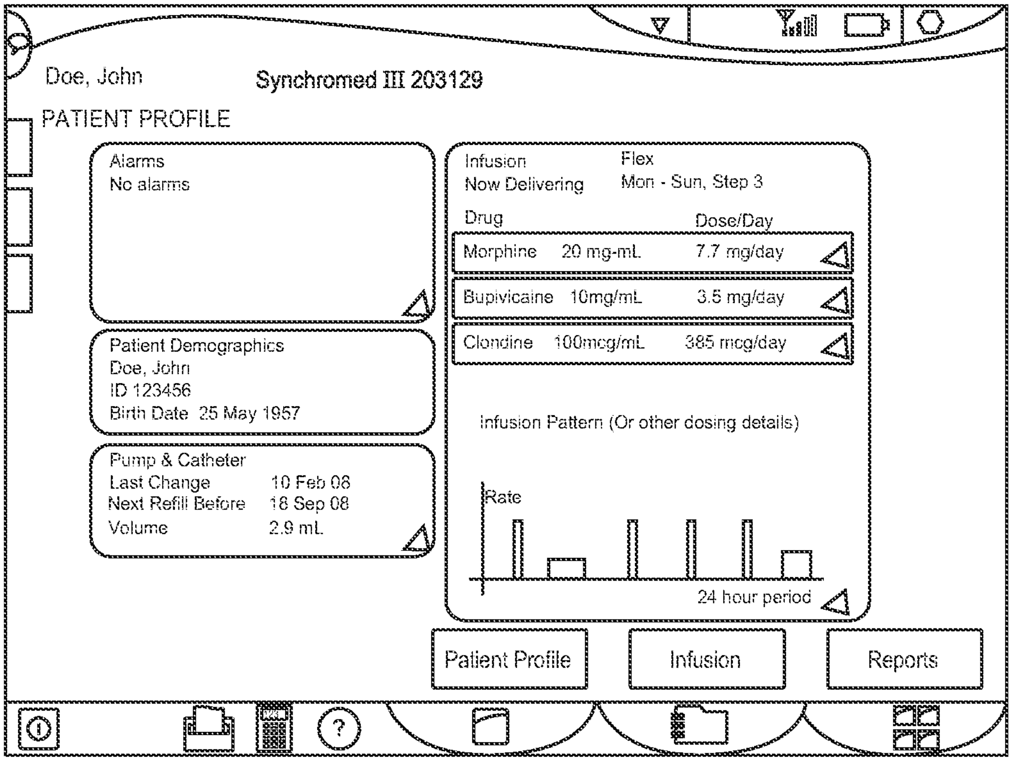
FIG. 11B illustrates another screen shot for displaying patient information.
Figure 11C:
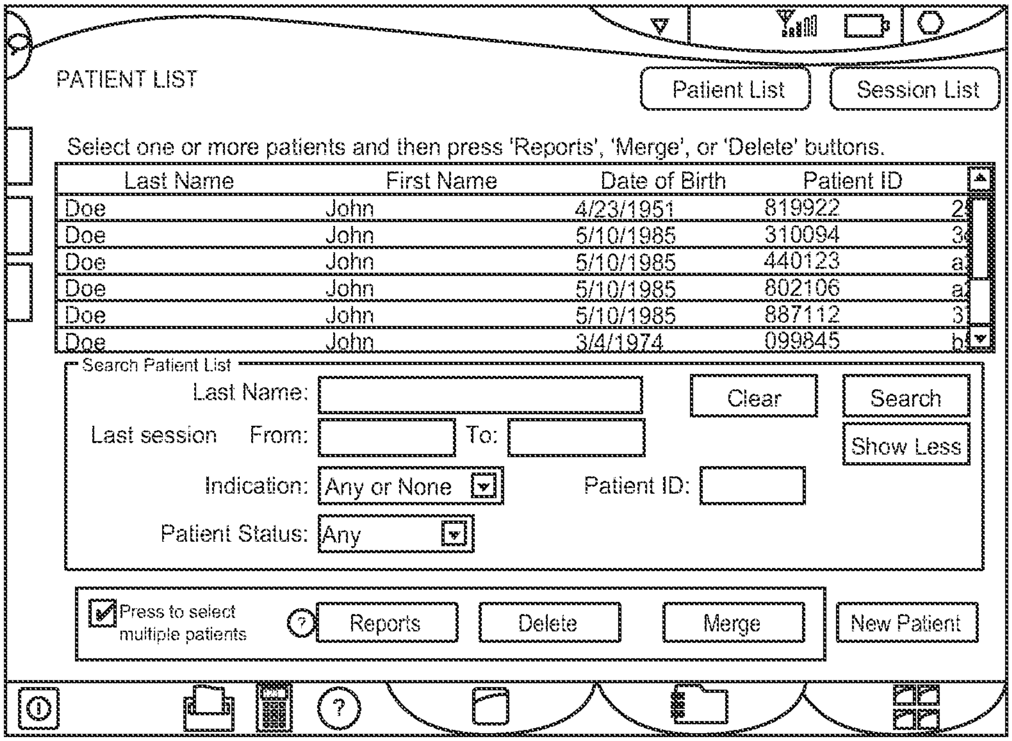
FIG. 11C illustrates a screen shot screen wherein multiple patients have been selected for displaying information.
Figure 12:
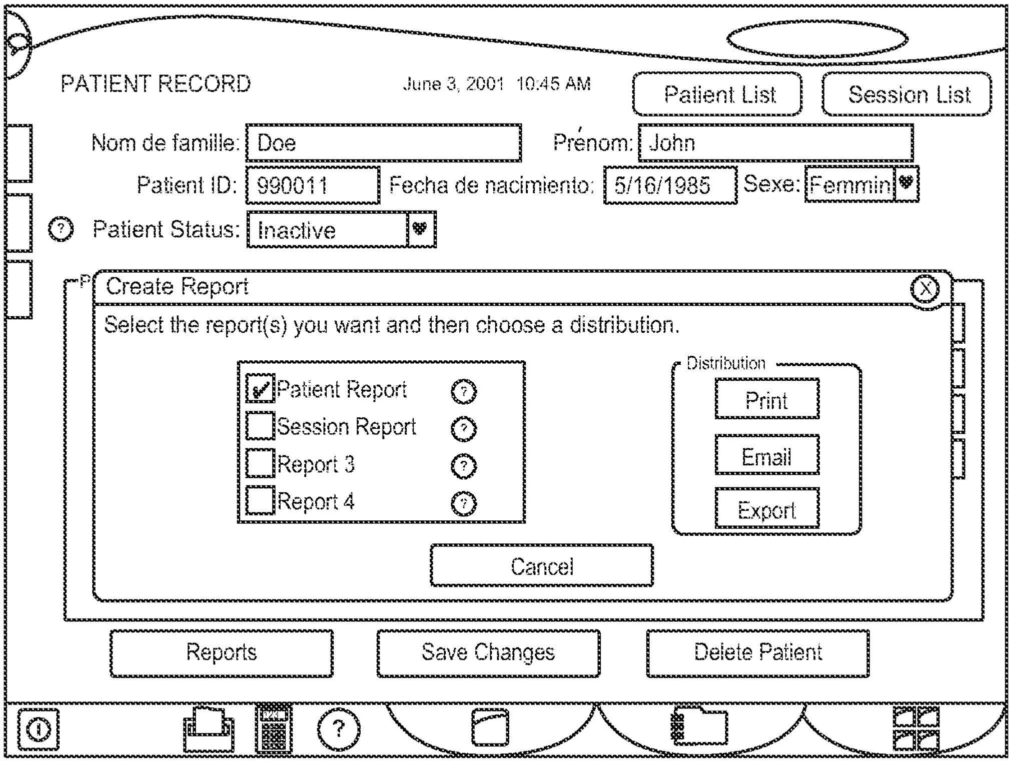
FIG. 12 illustrates a screen shot for creating a report.

Before the user begins a session by interrogating the implanted device 14, the user may select the patient's profile to pull up the patient's record, or, in other situations, the information may be pulled directly from the implanted device 14. As illustrated in FIG. 8, the patient's name or other information may be entered into the system 12 to pull up the patient's records. As illustrated in FIG. 10A, the patient may be found by entering the patient's name in a search box or by selecting the patient from an automatically populated list. FIG. 10B illustrates another screen shot for finding a patient using different search terms. A search may pull up a number of different possible patients from which the user must select. Further search terms may be likewise available on different screens (not shown). Selecting a certain patient may provide the user access to the specific patient's information, as illustrated in FIGS. 11A and 11B. FIG. 11C illustrates a screen shot wherein multiple patients are being selected from the patient list. The ability to select multiple patients may allow for certain types of reports or comparisons to be made. The user may then select to create a report, as illustrated in FIG. 12, or to do other operations, such as to enter new programming, which will be further discussed below.

Figure 13:
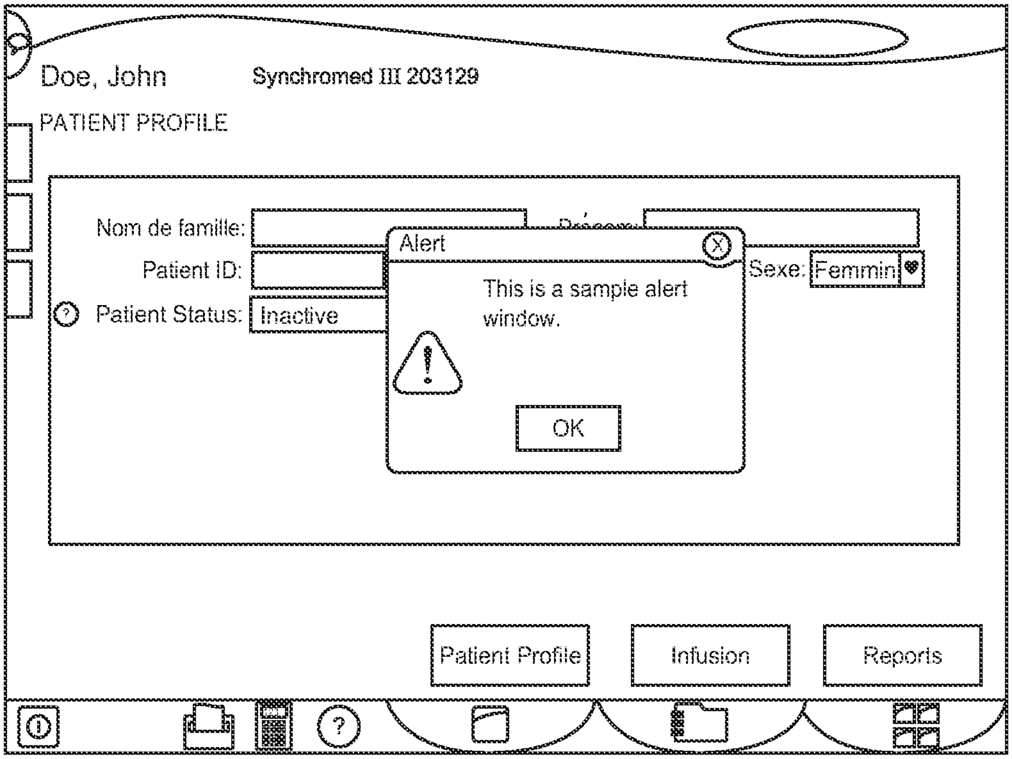
FIG. 13 illustrates a screen shot of an example alert window.

FIG. 13 illustrates an example alert window when the user has entered incorrect information or incorrectly selected an option. Alerts may be presented for a variety of situations, such as, for example, warnings related to low reservoir, pump error, memory error, and motor stall, or for other alerts specific to different devices 14.

Figure 14:
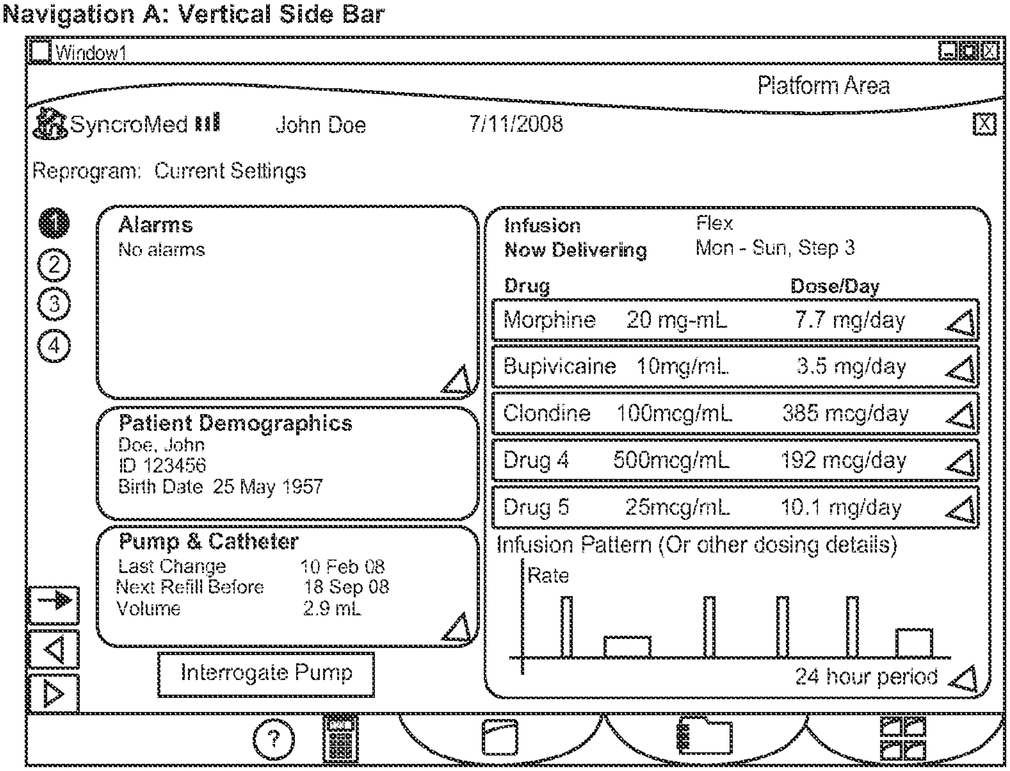
FIG. 14 illustrates a screen shot of a sample navigation display.
Figure 15:
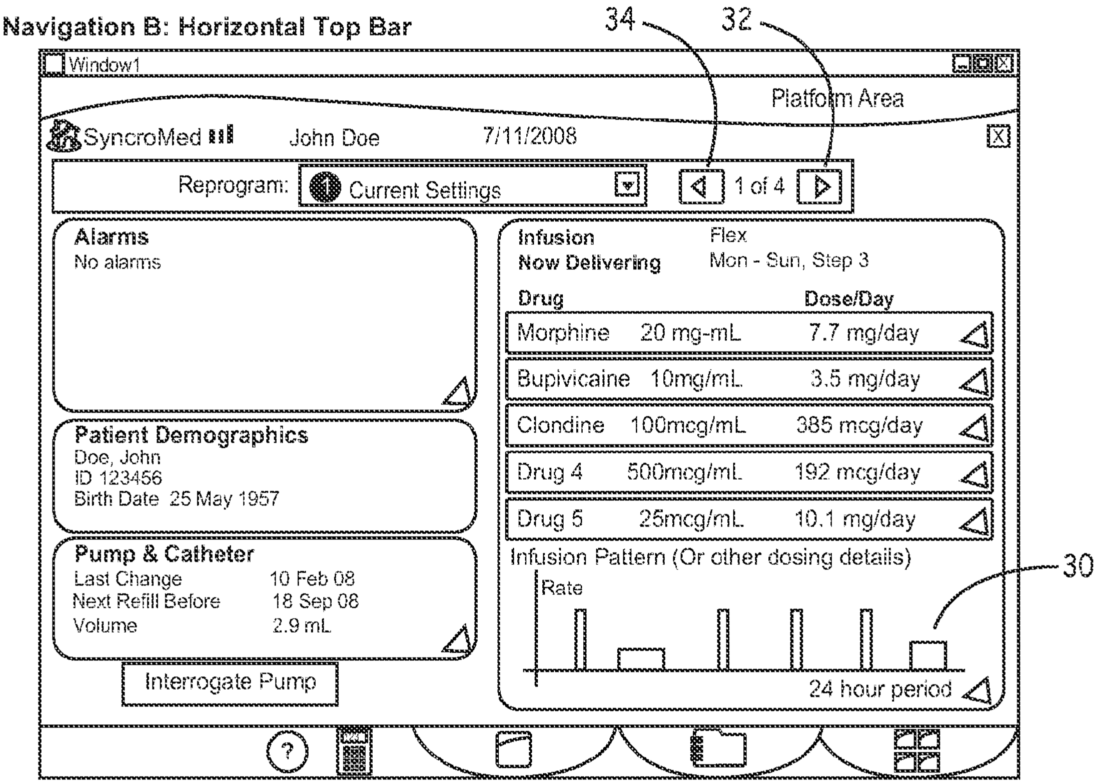
FIG. 15 illustrates a screen shot of another navigation display.

As may be appreciated, in a computer operating system a user may be presented with helpful information in a variety of ways. For example, in FIGS. 14 and 15, the user may be informed how many steps are required to complete a task and on what step the user is currently working. As shown in FIG. 14, the number of steps are shown on a vertical side bar with the current step shown in bold. This may include both numerical informational (the numbers) as well as visual type information (the number of bubbles). As may be appreciated, the user may, in some situations, select a step out of order by clicking on the link for that step. As shown in FIG. 15, the number of steps may be shown in a numerical manner and combined with a drop down menu or a simple option to page next or page back. The user may interrogate device 14 in a similar manner from either screen. In addition, each screen may present the user with the infusion pattern, or other dosing details, that are tied to the selected patient's record. Other selectable icons may likewise be presented to lead the user to other informational screens depending on the implantable device 14 type and the operating environment.

As shown in FIG. 15, a 24 hour dosage summary 30 may be illustrated in a graphical insert, also known as a sparkline. This summary may appear in all or a number of different screens presented by the programmer 20 to illustrate the general infusion pattern. In some situations the infusion pattern may be given without details on specific dosage amounts. In other embodiments more detail may be given on the summary to convey the duration or amounts. This interface not only provides the medical professional with summary view of the daily infusion program but also allows the medical professional to modify the infusion program while observing the summary view. Such summary information may be a helpful tool to the user to keep the general infusion pattern illustrated when performing various tasks. The sparkline can present data for one day, a week, or for any customizable period.

FIG. 15 illustrates forward and back buttons 32, 34. Selecting the forward 32 button may allow the user to proceed to the next task to be chronologically performed. Selecting the back button 34 may do the opposite, taking the user to the previous chronological task. Presenting the tasks in this order allows the user to keep progressing to the next task with the forward button 32 without having to think about which is the next proper chronological task.

In one embodiment, the task drop-down box may be a true drop-down box. When the drop-down is selected, the box may show all of the possible tasks that may be performed relating to the current screen, or at least more tasks than were pre-checked or individually checked at the initial procedure screen. This allows the user the flexibility of navigating to any task at any time.

The user may select to proceed with a task from a number of different screens by selecting the appropriate icon. Making such a selection may start a task based flow interface. Selections may include refilling the implantable device 14, uploading programming or software updates to the implantable device 14, uploading and downloading information to and from the implantable device 14, changing the infusion program, and combinations of these procedures and/or other additional procedures. The tasks associated with each procedure may be chronologically organized such that the first screen presented following the section is the first task that needs to be performed.

Figure 16:
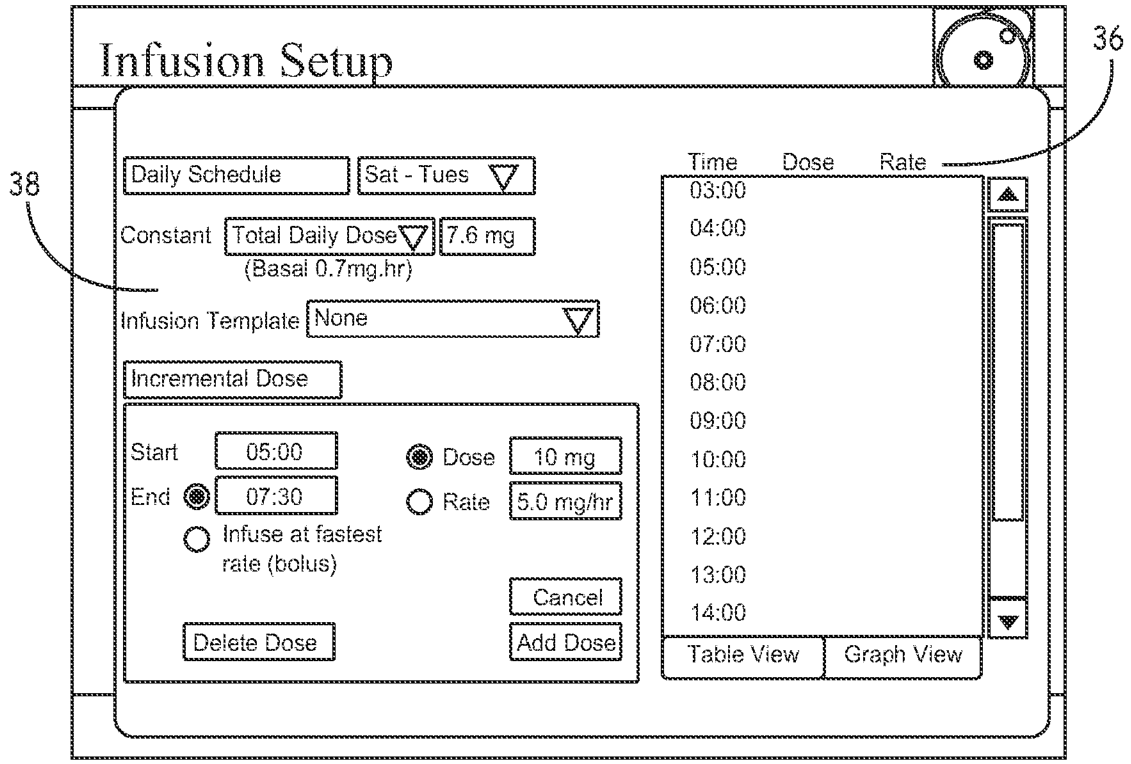
FIG. 16 illustrates a screen shot of a screen for creating an infusion program.

FIG. 16 illustrates a screen in which an infusion program may be entered by the user. The user may select or highlight a time frame and manually enter the dosing information by selecting the correct icon. Other icons may be utilized to adjust the total daily dose, the days for which the dose should be run, and other information. Entering the infusion program in this manner takes advantage of direct information input and will be considered non-graphical for purposes of this description. Once one or more doses are entered to create an infusion program the display may eventually look like FIG. 17.

Figure 17:
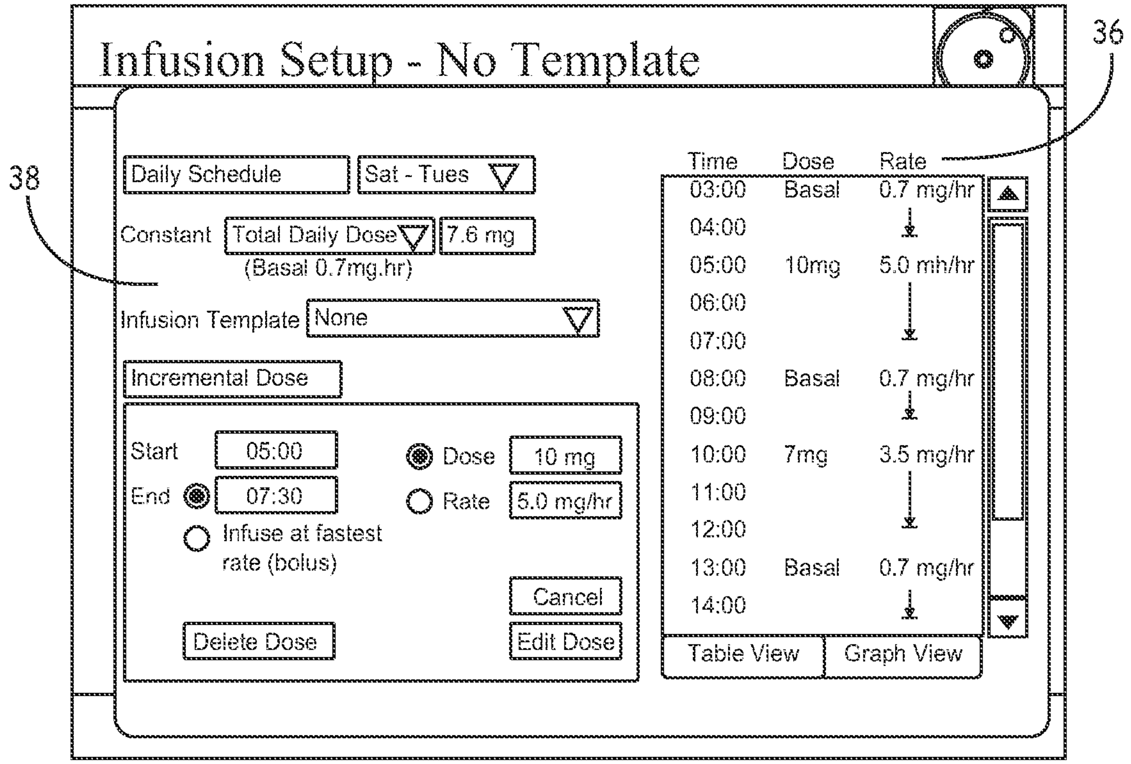
FIG. 17 illustrates a screen shot of FIG. 16 once an infusion program has been created.

In FIGS. 16 and 17, the time of day may be scrolled through on a first side 36 and the specific dosing information for a selected period may be presented and edited on a second side 38. A user may select specific dosing information to review or the user may scroll through the entire day's information. In addition, the user may decide to edit a selected dose by selecting a particular section of the first side 36 of the display. The infusion set up may present information retrieved based on the patient selected or from the interrogation of the pump. In addition, the user may view the dosing information in a graphical format by selecting the graphical view. Such a graphical view is further discussed below.

Figure 18:
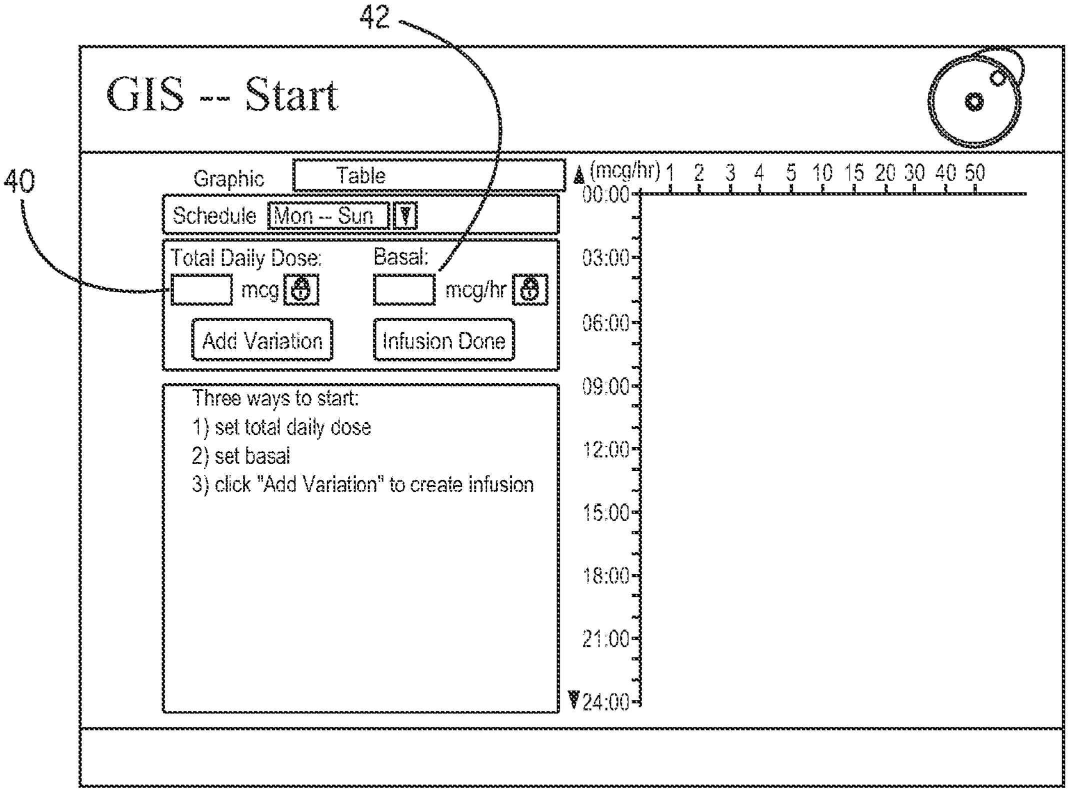
FIG. 18 illustrates a screen shot of another screen for creating an infusion program.

FIG. 18 illustrates another screen for presenting infusion data. FIG. 18, similar to FIG. 16, illustrates a blank dosing regimen into which information can be input. As illustrated, several ways of inputting information may be undertaken, including setting a total daily dose, a basal rate, or specific dosages for specific periods of time. Furthermore, the total daily dose or the basal rate can be locked or unlocked using icons 40, 42. A total daily dose rate could be entered and then as various other dosages are programmed, each already entered dose rate is adjusted to preserve the total daily dose at a locked amount. The basal rate can likewise be locked to insure a minimum (or maximum) rate is always present.

Figure 19:
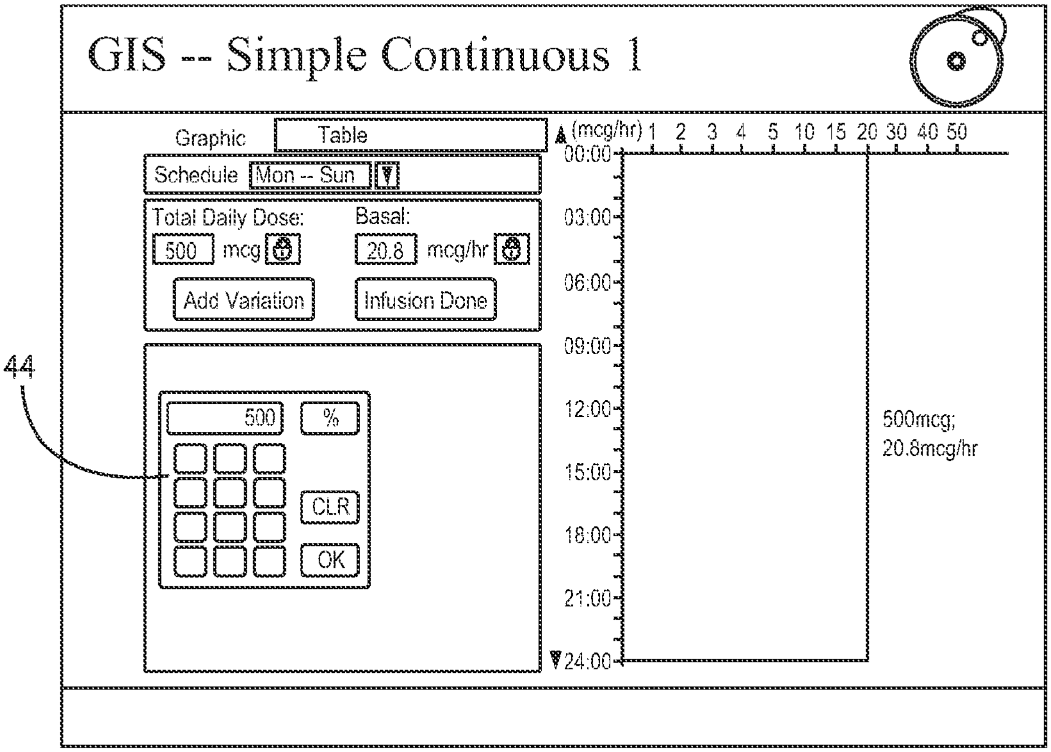
FIG. 19 illustrates a screen shot of FIG. 18 displaying an entered simple continuous infusion program.

In FIG. 19 shows a simple continuous dosage of 20.8 mcg/hour. In this screen shot the dosing information is presented in a graphical format showing 24 hours at the same rate. As illustrated, the user may change the dosing rate by increasing or decreasing the dosage on a percentage basis using icon 44 or by selecting the other icons 40 and 42. Changing the dosage on a percentage basis may be limited to a selected dosage range or all of the ranges simultaneously.

The graphical representation shows the hours of the day in the vertical axis and the dose per hour in the horizontal axis. In one embodiment, the exact amount programmed for each portion of the graphical representation is revealed by passing the cursor over the particular portion of the graph causing a pop-up to appear with the numeric information. The daily dose for each medication is shown in the right hand margin to provide the medical professional with up-to-date information of the total dosing amounts as the infusion is changed.

Figure 20:
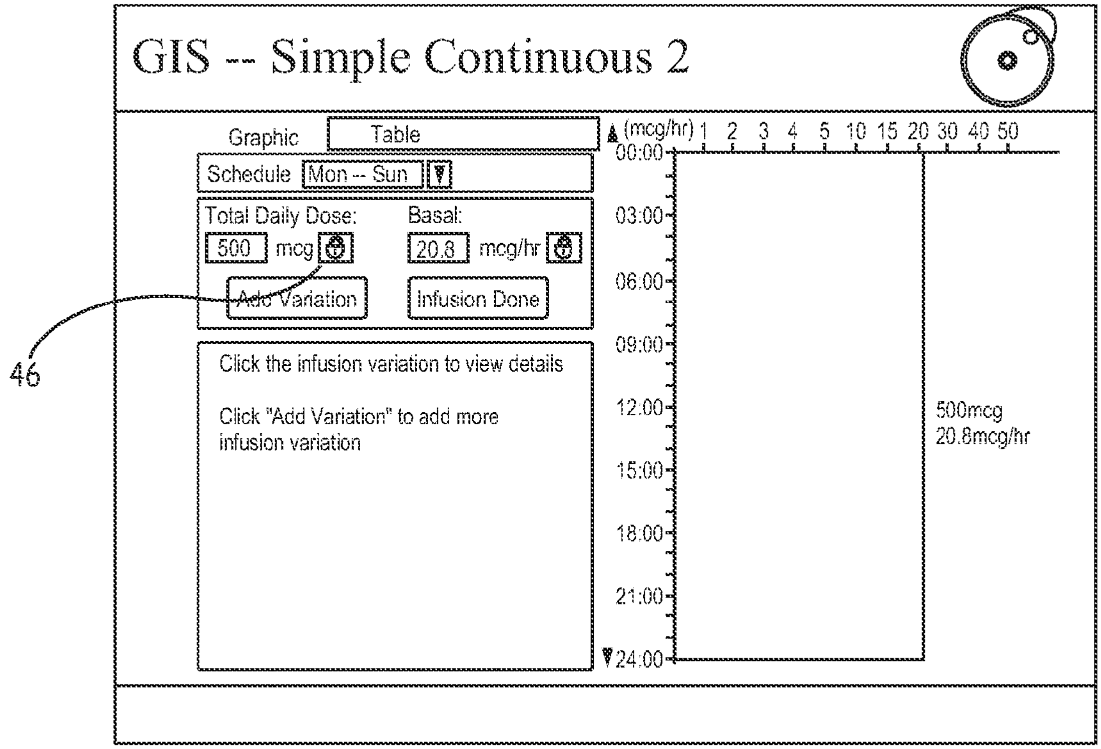
FIG. 20 illustrates a screen shot of FIG. 19 with the totally daily dose locked.
Figure 21:
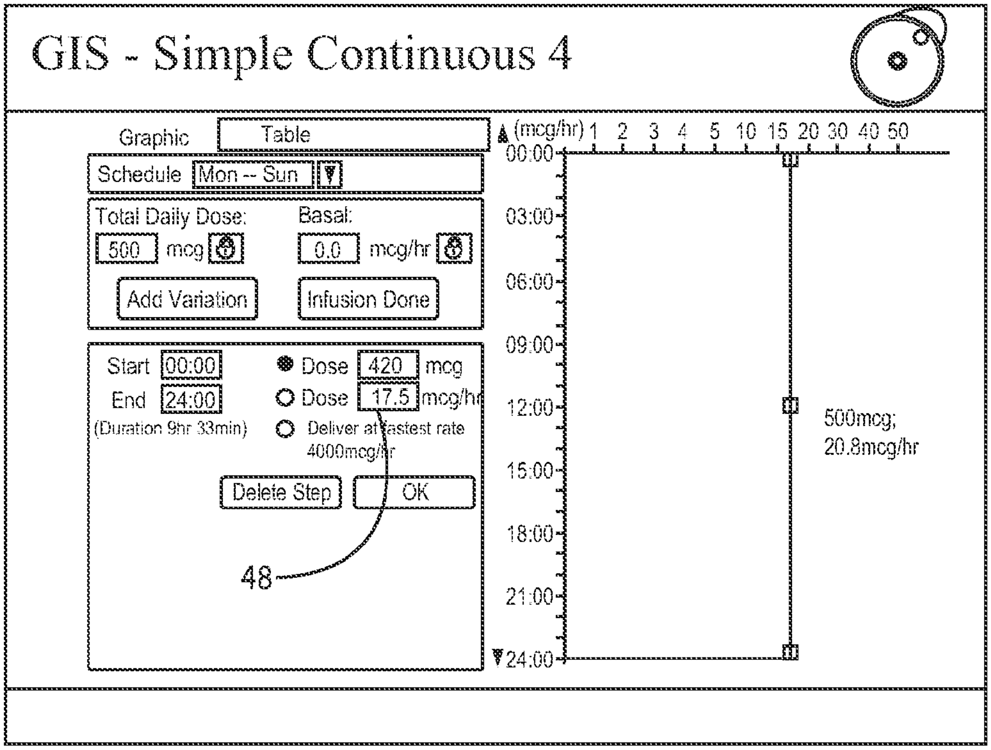
FIG. 21 illustrates a screen shot of FIG. 20 with the totally daily dose changed and the new rate calculated.
Figure 22:
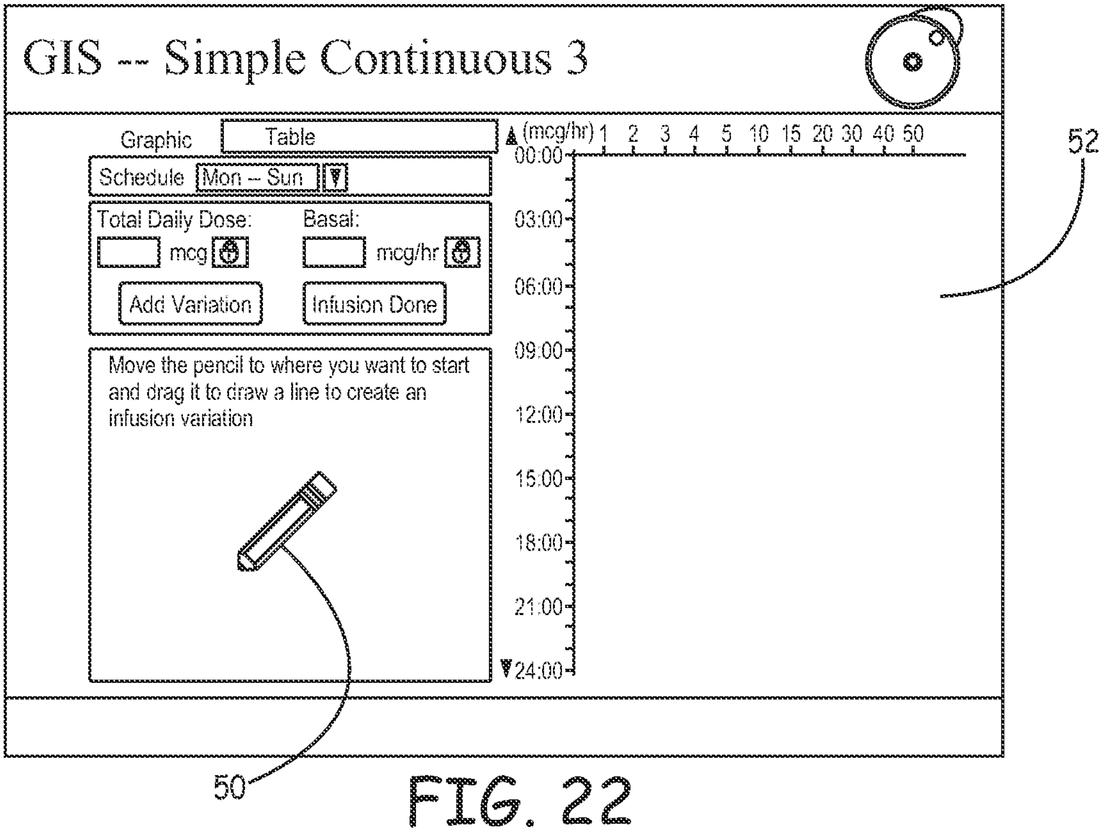
FIG. 22 illustrates a screen shot of another screen for creating an infusion program.

FIG. 20 illustrates the same dosing regimen shown in FIG. 19, with the total daily dose amount locked using icon 46. Instructions are also present that instruct the user to add variation to the dosing regime by selecting the icon that says "Add Variation." FIG. 21 shows the total daily dose amount unlocked and changed to 420 mcg. As illustrated, the rate to achieve this total daily dose is automatically presented at 48.

FIGS. 22-25 and 28*a-d* illustrate another method of inputting dosing information or editing the already existing information. The method may include the use of a pencil 50 displayed on the screen. As may be appreciated, the method may also utilize a light pen, a peripheral pointing device, or any other type of pointing device for a user to input information into a computer, such as a touch screen, pen top computer, or a mouse. In the illustrated example, the user may engage the pencil 50 (or any other icon that is selected) and move it to a graphical drawing tablet 52 on the screen, where infusion information will be input. Various combinations of selecting the pencil 50, dragging it, and releasing it in the graphical drawing tablet 52 to draw may be utilized. In one example, the pencil 50 is selected and then moved to a location to begin drawing. The pencil 50 may then drop down to a writing position. As may be appreciated, various colors, highlights, or other indicators on the pencil 50 icon may illustrate when the pencil 50 is dropped down (engaged) or picked up (not engaged) for drawing. In further embodiments the user may use a light pen or a stylus to draw directly on the screen of the programmer 20. Furthermore, the pencil 50 may be utilized to create a number of different infusion programs, such as, for example, simple continuous, day/night, and flex, in addition creating boluses and other variations in the pattern.

Figure 28A:
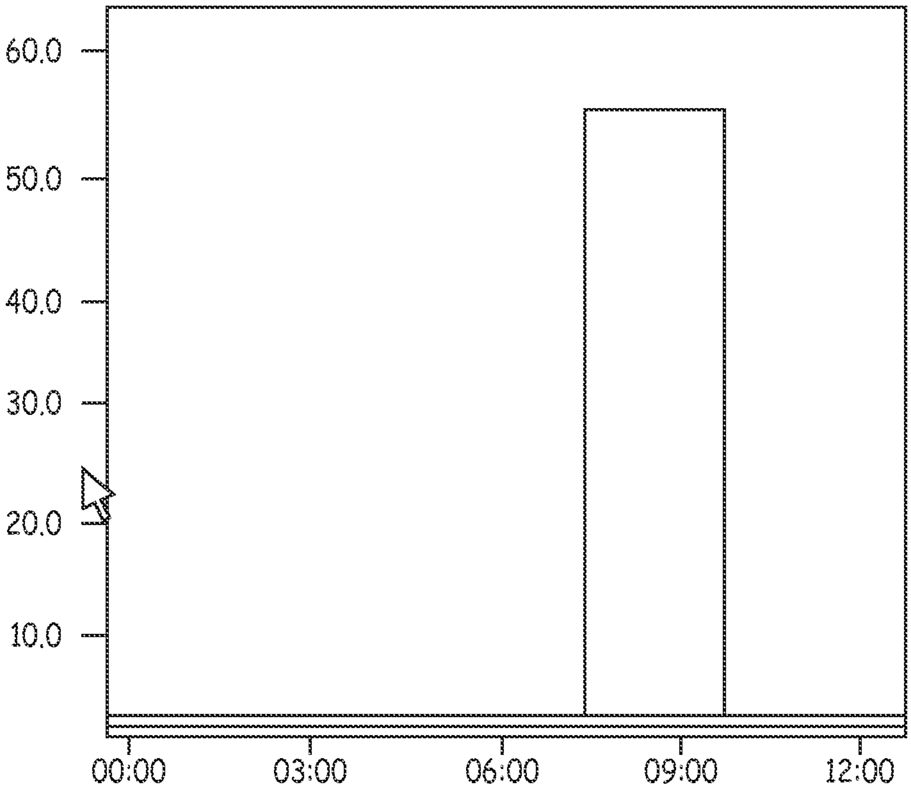
FIG. 28*a-d* illustrates screen shots of graphically creating a new dosage.
Figure 28B:
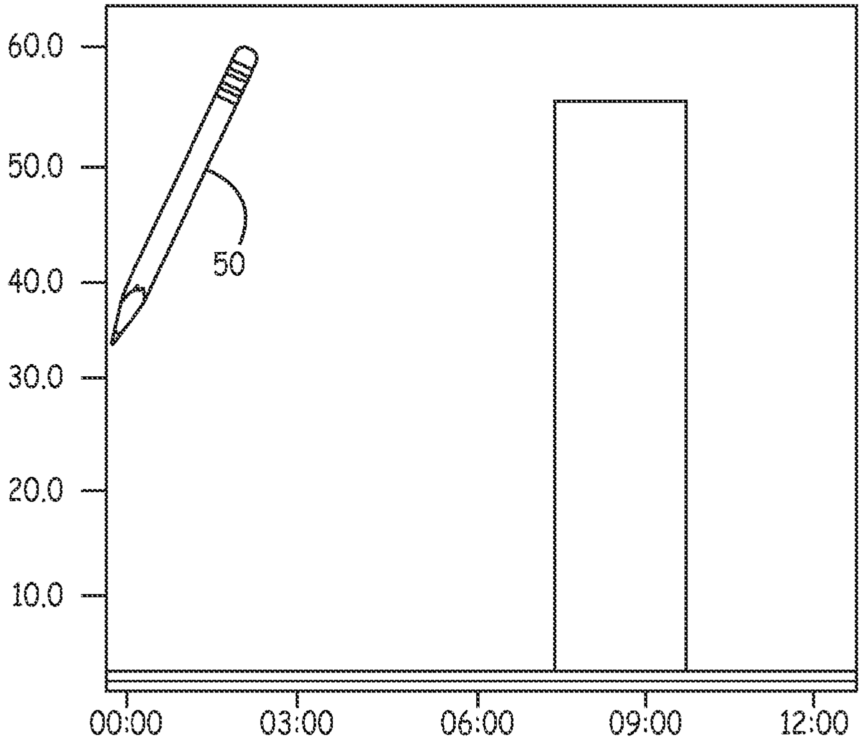
Figure 28C:
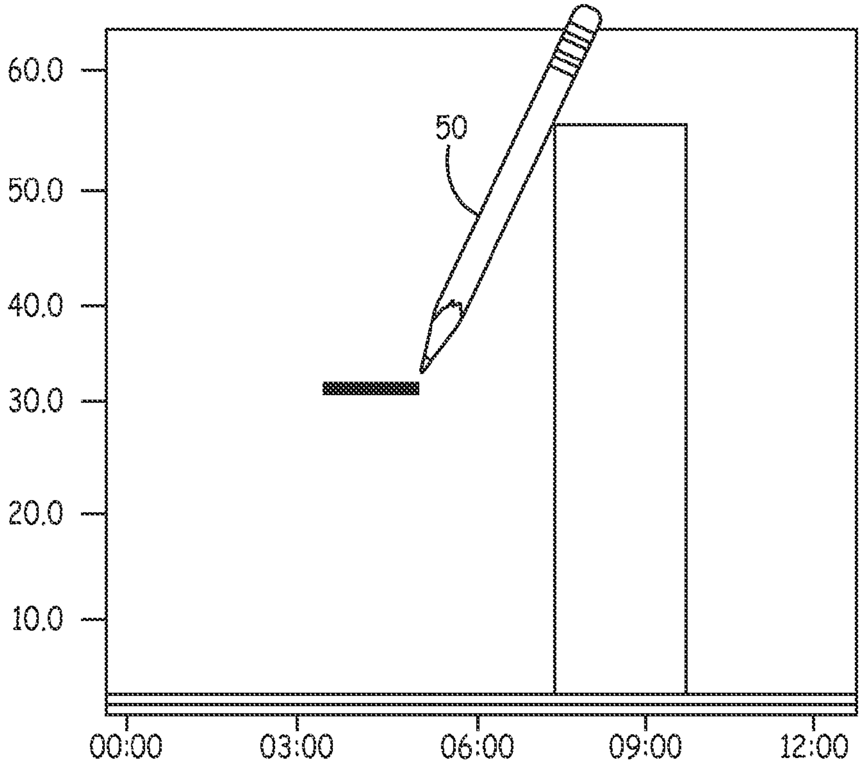
Figure 28D:
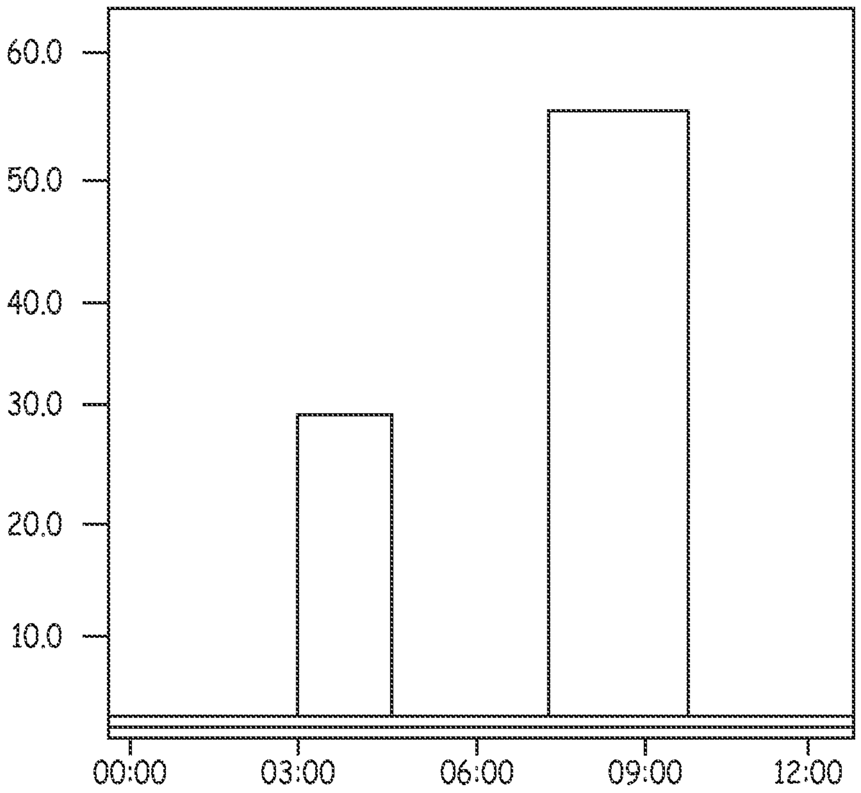

FIGS. 28*a-d* illustrate one example of using the pencil 50 to draw an infusion program. FIG. 28*a* illustrates a twelve hour time period wherein the dosage from about 08:00 until 10:00 is already programmed. The user may engage the pencil 50 and bring it into the graphical drawing tablet 52 as shown on FIG. 28*b* and thereafter engage and drag the pencil 50 along the dosage rate for the time for which the new dosing is to take effect. (Though FIGS. 28*a-d* are oriented different than the graphical drawing tablet shown in FIG. 22, it does not change the general description put forth herein.) As illustrated in FIG. 28*c*, electronic "ink" strokes appear where the user has drawn using the pencil 50. When the user disengages the pencil the programmer 20 may interpret the line and create an infusion pattern as illustrated in FIG. 28*d*. Multiple lines may be created on the graphical drawing tablet 52 at one time before the programmer 20 fits an infusion program to the inputted data. In other embodiments, the user may input one line at a time on the graphical drawing tablet 52 and ask the computer to interpret each entry as a separate dose before making a subsequent entry. As will be explained further below, the user may then edit the dosing pattern in a variety of ways.

Figure 23:
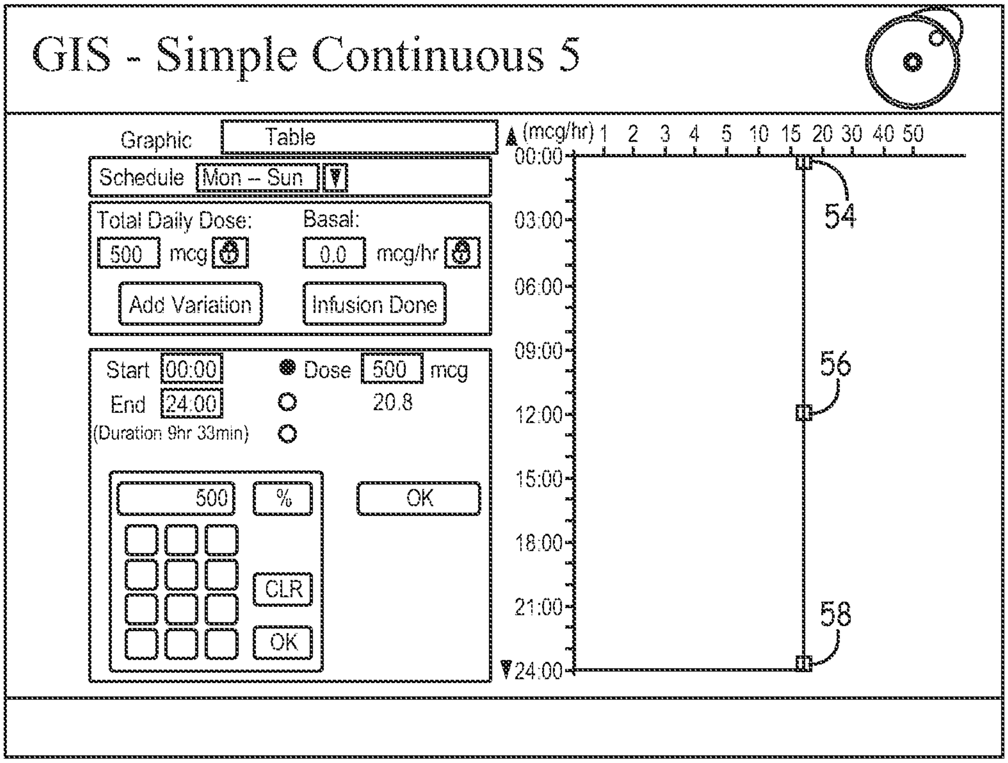
FIG. 23 illustrates a screen shot of FIG. 22 with the infusion program entered.

The presently described programmer 20 therefore allows for electronic ink strokes to be used to graphically create the infusion program. The programmer 20 may utilize an algorithm to interpret the ink strokes and translate them into therapy settings. In various embodiments, the programmer 20 may interpret the ink stroke line in various ways according to pre-set rules, such as using rectilinear patterns. The programmer 20 may be set to interpret the dosage at the first ink stroke level, the last level, or some calculated statistic related to all the levels input. In some embodiments, the programmer 20 may correct or ignore inappropriate or imprecise marks. In certain situations, for instance, the user may overlap different strokes or may not draw the line straight enough to be interpreted as one dose. In further embodiments, when a dosage level is created when the ink stroke is started, the user may only be able to draw a level dose such that the continued action of dragging the pencil 50 to draw only controls the dose duration. In other embodiments the programmer 20 may be set to allow for dosages that include curves or slanted lines to represent constantly increasing or decreasing rates. Such non-rectilinear dosages may include a best curve fit feature. Various other types of checks and balances on how the information is input may be implemented by one of ordinary skill in the art, in addition to being user defined FIG. 23 illustrates a screen on which the simple continuous dosage illustrated in FIGS. 19-21 has been inputted using the graphical method described above. The programmer 20 has interpreted the dosing pattern to be 20.8 mcg/hr. The dosing pattern can be modified by clicking on any of the three boxes 54, 56 and 58 and expanding or contracting the shape of the box along various axes, such as an x-axis or a y-axis, thus changing the dose amount or dose duration. In this particular screen shot the dosing pattern can be changed to increase the dosing rate for the entire 24 hour period by clicking on box 56 or the dosing can be shortened from either end by clicking on boxes 54 or 58. The boxes, such as boxes 54, 56, and 58 may be referred to by different names such as anchors, and could be circles, rectangles, or any other type of selectable icon. Furthermore, the boxes 54 and 48 on the end of the dose may be utilized to expand the dosage in multiple directions such that the time and also the dosage level can be changed simultaneously.

Figure 24:
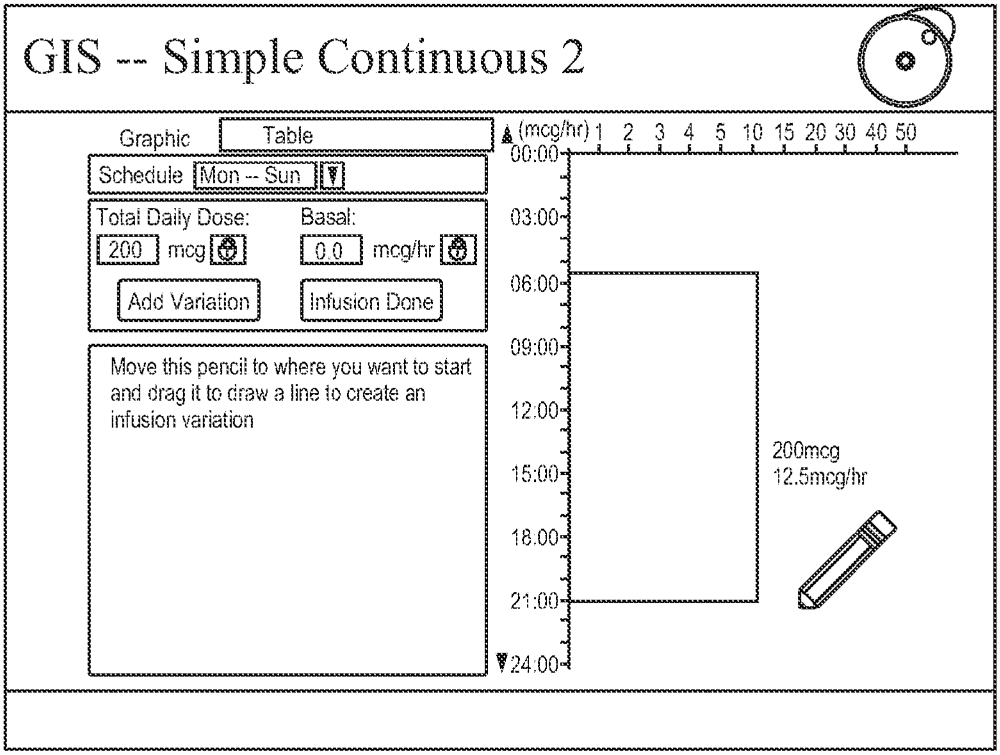
FIG. 24 illustrates a screen shot of another screen for creating an infusion program.
Figure 25:
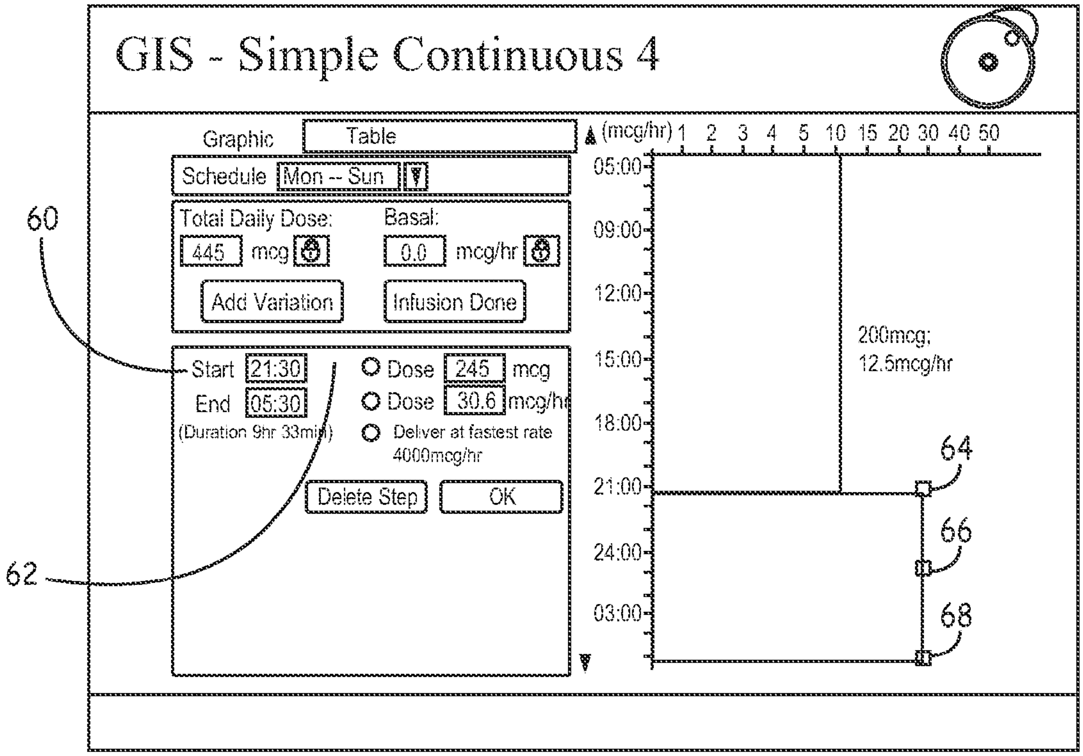
FIG. 25 illustrates a screen shot of FIG. 24 with the infusion program entered.

FIG. 24 illustrates a dosage of 200 mcg at 12.5 mcg/hr from 06:00 to approximately 21:00 as a first entered dose with the pencil 50 ready to start drawing a second dose from 21:00 onwards. In FIG. 25 the pencil 50 has been utilized to draw the second dose from 21:30 to 5:30 and the programmer has filled in the dose as interpreted. In the present example the line was drawn (not shown) generally vertically along the dosage rate desired (in this case, 30.6 mcg/hr) and for the desired time period, which was then interpreted by the programmer 20 as shown in FIG. 25. A summary of the dosage rate and time period as interpreted by the programmer 20 may be displayed numerically in icons 60, 62. As previously discussed, the dosage may be changed as desired by adjusting the rate or the time duration either graphically or numerically. To change the dosage information graphically the user may use a mouse or other input device to select one of the boxes 64, 66, 68 to change the amount or duration of the dose by changing the shape of the box as along an axis as previously described. In further embodiments, the user may select boxes for one or more of the rates, or all of the rates, and change the rates concurrently. For example, if two therapy rates as shown in FIG. 25 are selected together, both can be made larger or smaller together. In further embodiments the dosages may change based on a total daily dose whereby when one or more dosages are increased or decreased, the remaining doses decrease or increase a proportionate amount to maintain the total daily dose.

Figure 26:
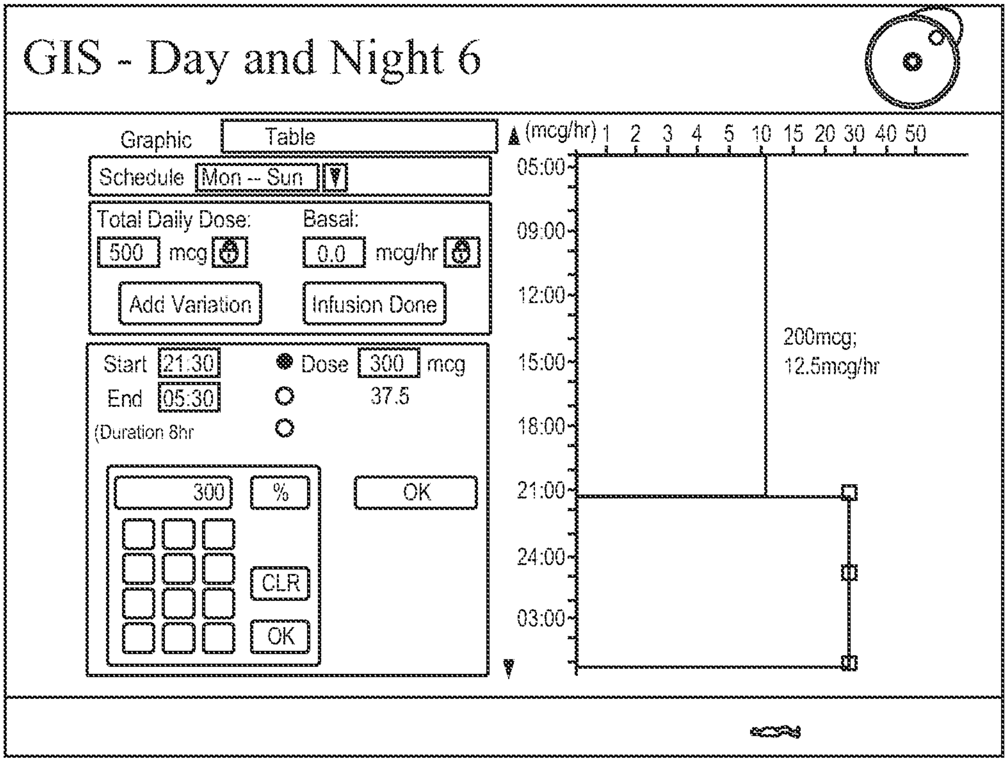
FIG. 26 illustrates a screen shot of FIG. 25 with the infusion program edited by numerically inputting a new total dose.
Figure 27:
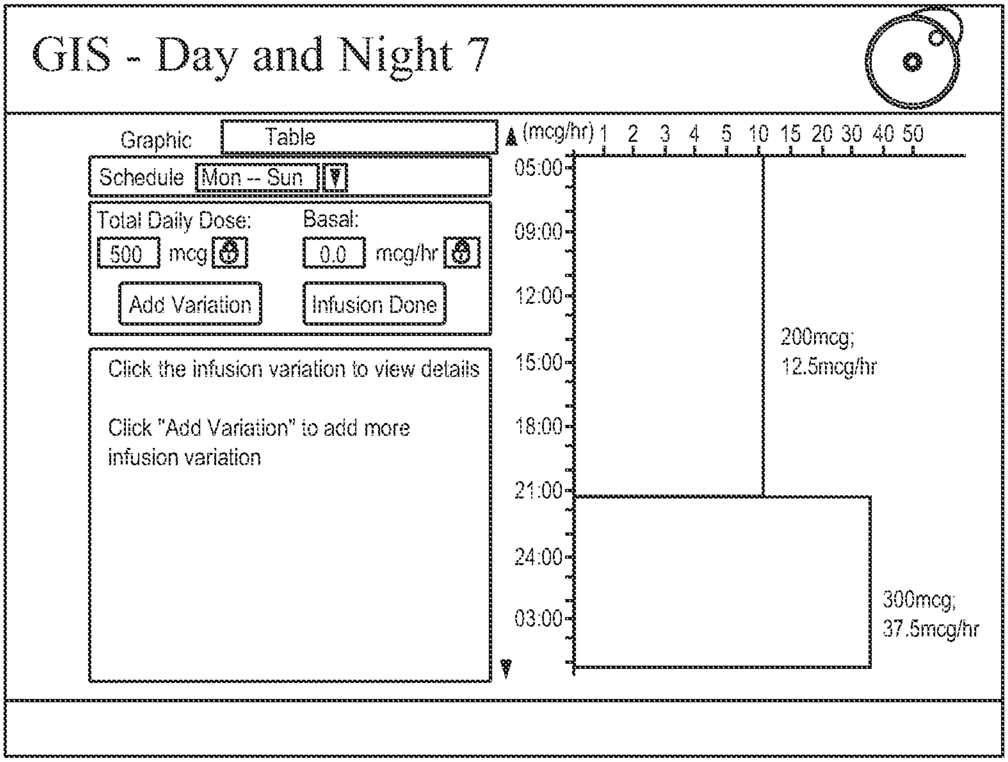
FIG. 27 illustrates a screen shot of FIG. 26 with the newly entered dosage information illustrated on the graphical display.

To change the information numerically the user may click on one of the icons 60, 62 and numerically enter in a new rate, total dose, or duration. FIG. 26 illustrates the user changing the dosage entered in FIG. 25 by entering a new total dose of 300 mcg for the still selected time period. The programmer 20 then calculates the new dosage rate as 37.5 mcg/hr. FIG. 27 illustrates the completed dosage entry. In the illustrated figures the dosage rates may not be illustrated proportionally, though, in other embodiments, the rates may be proportional to provide quicker and easier identification of relative rates.

Figure 29:
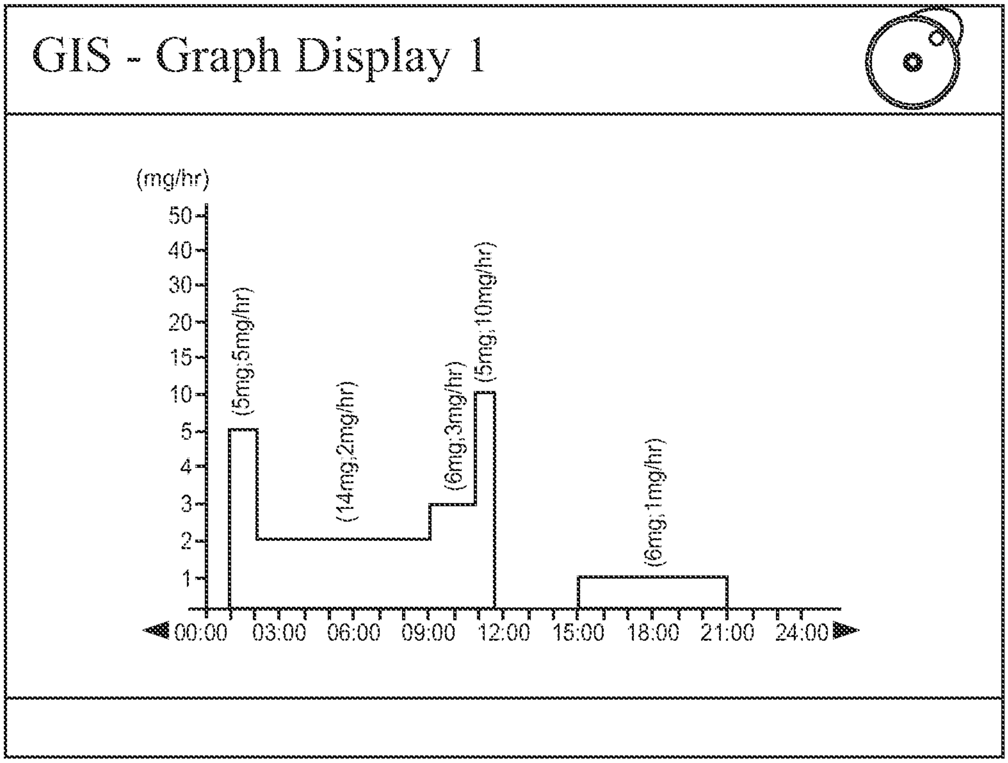
FIG. 29 illustrates a screen shot of an infusion program.
Figure 30:
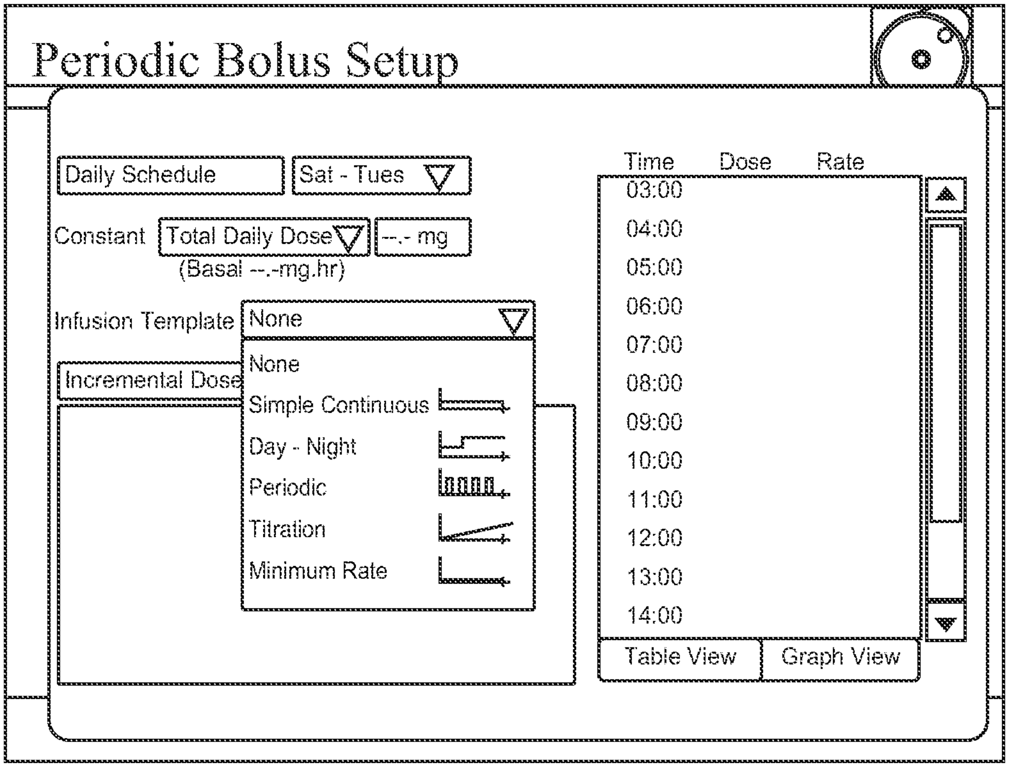
FIG. 30 illustrates a screen shot of another screen useful in creating an infusion program.

FIG. 29 illustrates a screen shot wherein the programmer 20 has been programmed with several different dosing levels and times. Such a dosing regime may be easily created using the ink pen method described above. In some situations, the various dosages may be too small to be selectable using a pointer and so may not be easily edited using the graph mode. In such situations the information displayed on FIG. 29 may be instead displayed in a table format. Alternatively, the pointer may expand the individual doses automatically using a standard mouse over type system. In still further embodiments, the graph may not be displayed on one screen because of the relative sizes of certain rates versus other rates, such as a bolus being so large as the rate information extends off the screen. In other embodiments the programmer 20 may auto fit a scale to the screen to display all the information FIG. 30 illustrates a drop down screen that may assist in the creation of a dosing regime. Various types of templates may be selectable from an infusion template drop down menu. Such templates may assist in creating various dosing regimes. Further dosing regimes may be utilized by those skilled in the art, such as steps, gradients, combinations of steps and basal rates, periodic rates, and others. Other types of tool boxes of this type with a variety of templates may be presented to the user in such a format, such as, for example, slow or fast steps, basal rate steps, high rate steps, etc.

A day-night drug infusion program may also be programmed. As with a simple drug infusion program, the programmed dosages may be input through a graphical interface in which the user may draw on the screen using the selected peripheral input device. The user may then graphically view the dose and modify the dose by clicking and dragging the dose to a different dosage or duration. The difference is that the day-night drug infusion program contains two components, a day component and a night component. Note that the user may individually drag either the day or night segment to increase or decrease the dosage or to change the duration of the day or night. In still further embodiments, the day or night may be changed by the user and then the other field, night or day, may be automatically changed by the programmer depending on previously input total daily dosages.

Figure 31:
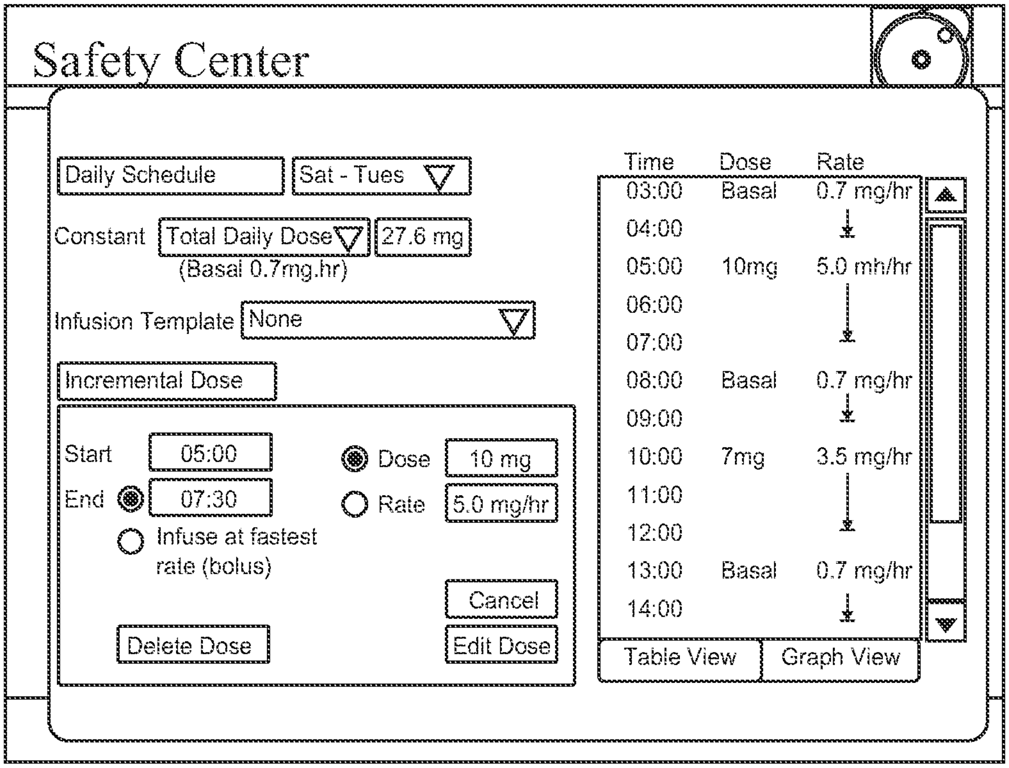
FIG. 31 illustrates a screen shot of total dose change warning.

In one embodiment shown in FIG. 31, the programmer 20 may display to the user a total percentage change of the therapeutic output as a result of any changes made by the user to the infusion program. The programmer 20 displays the percentage change before making any such changes effective in the implantable medical device. Such a screen may warn the user as to whether the overall percentage dose change is within reason before downloading the new dosage schedule to the implantable device 14. In certain embodiments the dose change may be highlighted by color, bold text, or through other indicators. In still further embodiments, the programmer 20 may require that the user confirm the percentage dose change is correct by clicking to close the notice before proceeding with the download. An extra click step may be implemented when the total daily dosage changes by greater than a preselected amount. In still further embodiments the programmer 20 may require a confirmation when a certain bolus or a selected dose is changed by more than a threshold amount.

If a bolus is desired, the medical professional may click in the open area of the graphical representation at a time where the bolus is desired to begin and drag the cursor down to the time where the bolus is desired to end. As the cursor is released, a new graphical segment is created which itself may be dragged left or right to obtain the desired amount of bolus. In either case, the dosage rate may be changed, or the start or stop times of boluses may be changed by clicking and dragging the cursor on the graphical representation.

As previously discussed, the programmer 20 may also include a screen for printing reports, such as an infusion program summary and/or other information. One example screen for reporting is shown in FIG. 12. The medical professional may print, e.g., to a hard copy or to a file or disk or message, a report of the information programmed in programmer 20. Thus, the program information may be retained for future reference. In further embodiments the programmer 20 may create and enable direct printing of reimbursement reports. As may be appreciated, reports may be transferred directly to another computer, e-mailed, printed, or saved to other databases. Such transfer of information should be in encrypted format where necessary and comply with the relevant laws and regulations. In addition, individual screen shot prints and downloads may also be available.

Once the program information is complete, the programmed information that is necessary for the implanted medical device 14 to operate, and any other desired, can then be sent, for example, by telemetry through the remote device 24 to the implanted medical device 14 and the new programmed amounts and features become effective.

In another embodiment, a screen shot (not shown) may allow the user to pick a total daily dose before beginning the creation of the infusion program. The programmer 20 may continually update the total dose entered in various individual dosages to keep the user informed of how much of the total daily dose is left available for implementation.

In still further embodiments, the user may be able to change when the "day" starts for purposes of programming. Changing the day and night settings may simplify programming. As part of this change, when the user is using the graphical user input device to lengthen a dosage time period the display may scroll past 0:00 or 24:00 to enable the user to program outside of a strictly 24 hour cycle.

In still further embodiments, a programmer 20 may be utilized to set up template therapeutic infusion days such that different pre-programmed days may be initiated from a patient programmer. For example, exercise days could be programmed different from work days or travel days and then selectable by the patient.

In certain embodiments the programmer 20 may be forced to round up or round down an inputted dosage amount. In the context of drug infusion pumps, the pump may only be able to infuse material at a fixed number of rates. Therefore, if the user graphically inputs an infusion rate that is not achievable by the pump, the pump may be required to round the dose to the nearest possible infusion rate.

In further embodiments the pencil 50 icon may also be paired with an eraser icon (not shown) such that the user can erase portions of the information graphically entered on the graphical drawing tablet 52 before asking the computer to interpret the information.

Figure 32:
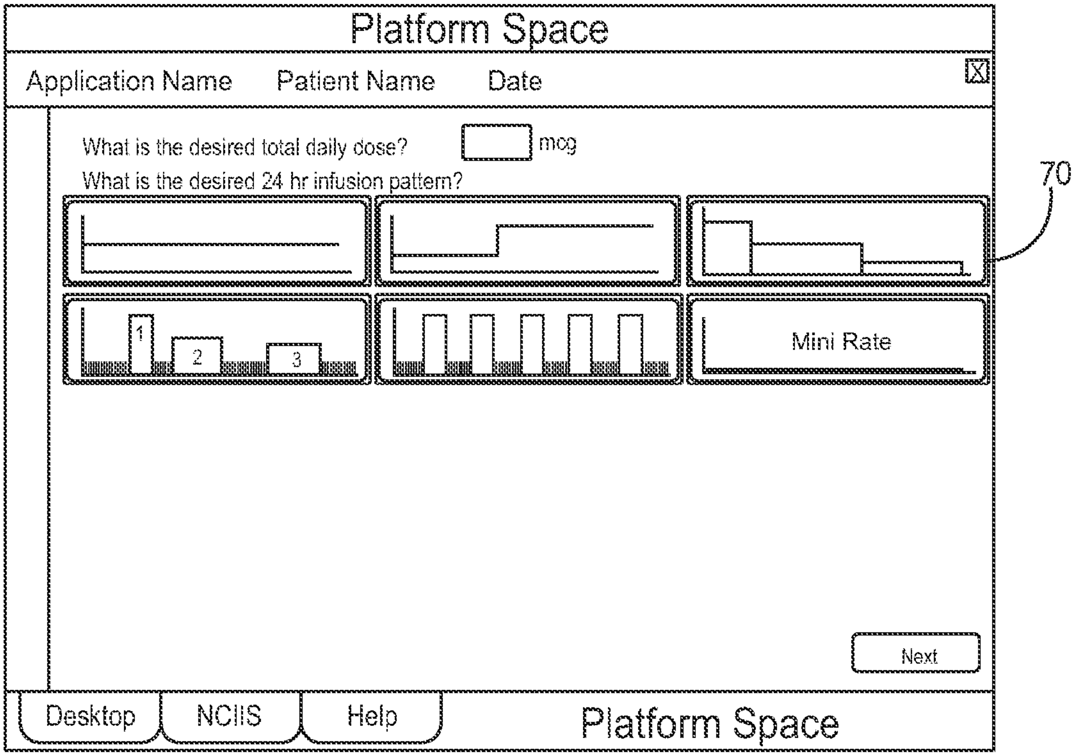
FIG. 32 is another screen shot showing a screen for programming an infusion program.

FIG. 32 is a screen shot of another embodiment programming screen. The illustrated screen gives similar programming options to the templates illustrated in FIG. 30. The templates in this embodiment may be displayed in a different menu. As with FIG. 30, the templates may be selected by the user to help enter an infusion program.

Figure 33:
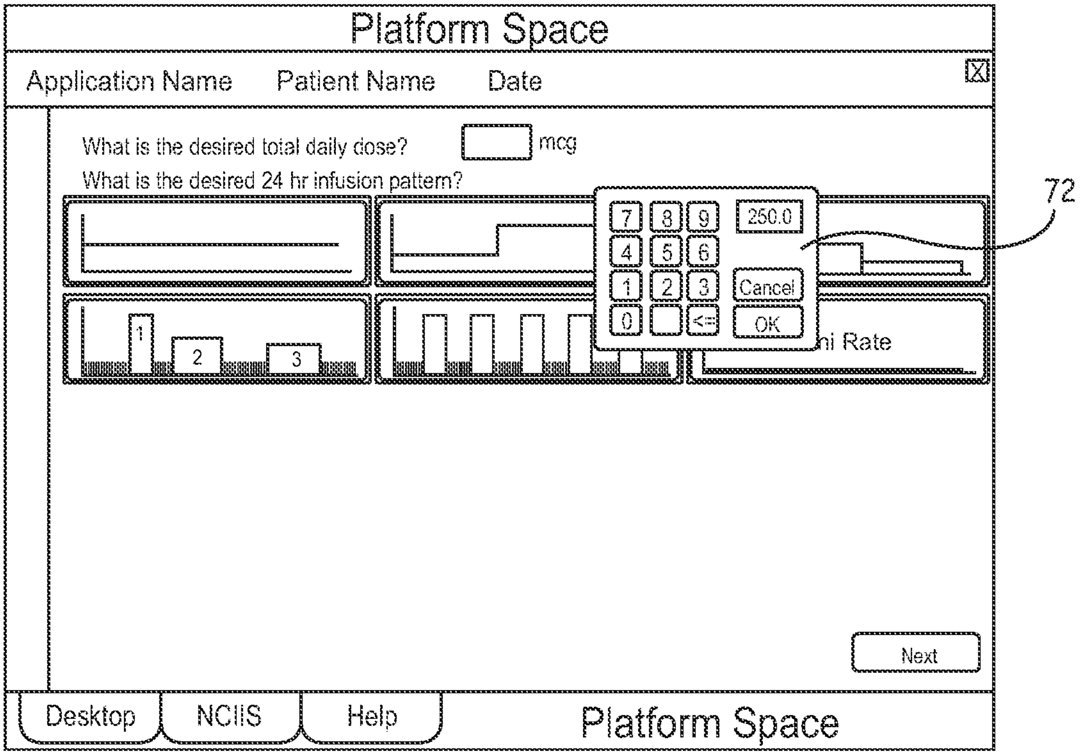
FIG. 33 is a screen shot of the screen of FIG. 32 with a total daily dose entered using a pop-up window.

Before or after the user has selected a template in FIG. 32, the user may be required to enter a totally daily dose in a pop-up window 72 as illustrated in FIG. 33. The pop-up window sown here is a keypad where numbers can be entered by touching the screen or typing numbers using a keypad on the programmer 20. As may be appreciated, the user may also, in alternative embodiments, select a template and then proceed without entering a desired total daily dose.

Figure 34:
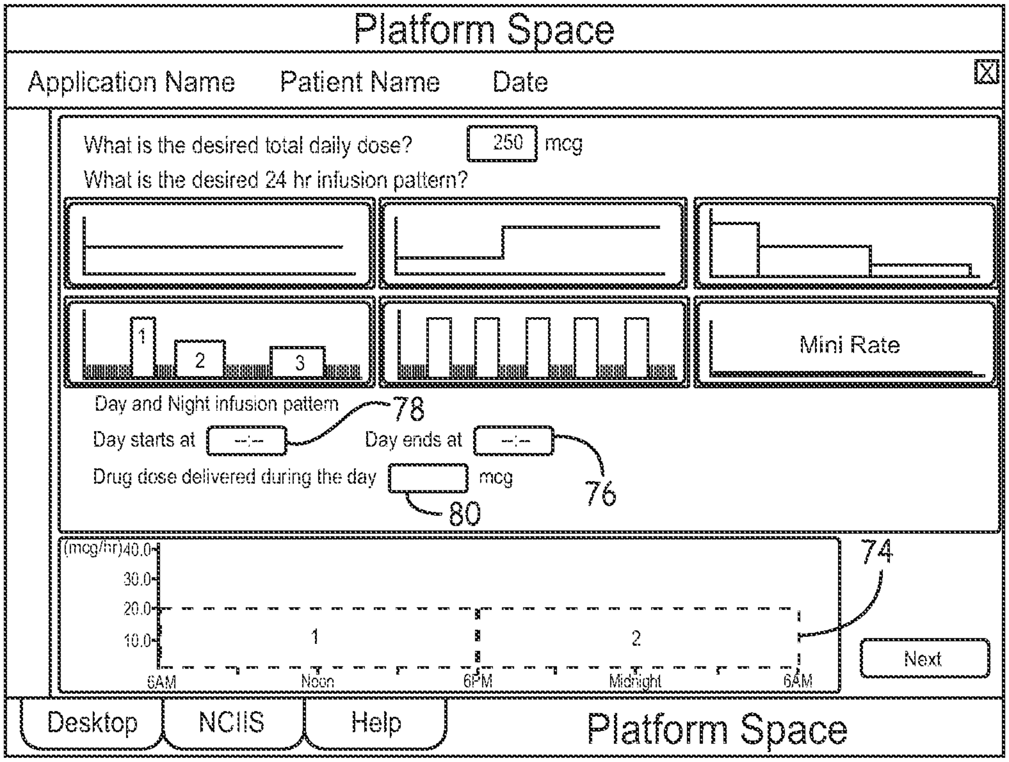
FIG. 34 is a screen shot showing the programming of a day and night infusion pattern.

FIG. 34 illustrates the programmer utilizes the selected template from the previous screen shot, selected as a day and night infusion program, and the totally daily dose information previously input, 250 mcg, and displaying a basic infusion program in a graphical format 74. The graphical display of the infusion program 74 is displayed in broken line format as the infusion program is tentative. The dosage pattern may be tentative because not enough data has been entered to consider it final, or ready for controlling the therapy provided by the infusion device 14. The tentative infusion program includes a basic program based upon the limited information that has been input and has not yet been edited by the user or populated with enough information to be finalized. For example, the infusion program illustrated does not show a variation between the day and night dosages because that information has not yet been entered. However, this screen may present the user with icons for entering the start period for the day and night infusion program 76, 78 as well as an icon for entering the drug dose to be delivered during the day 80. In alternative embodiments, the user may have the option of entering the drug dose to be delivered during the night portion of the infusion program. However, once the day or night dosage is entered, the corresponding drug dose can be quickly calculated by the programmer 20 if the user has previously entered in the desired total daily dose. In addition, the programmer 20 may continually update the amount of the target total daily dose that has been utilized by the entered dosages or how much is left to utilize as the dosages are entered.

Figure 35:
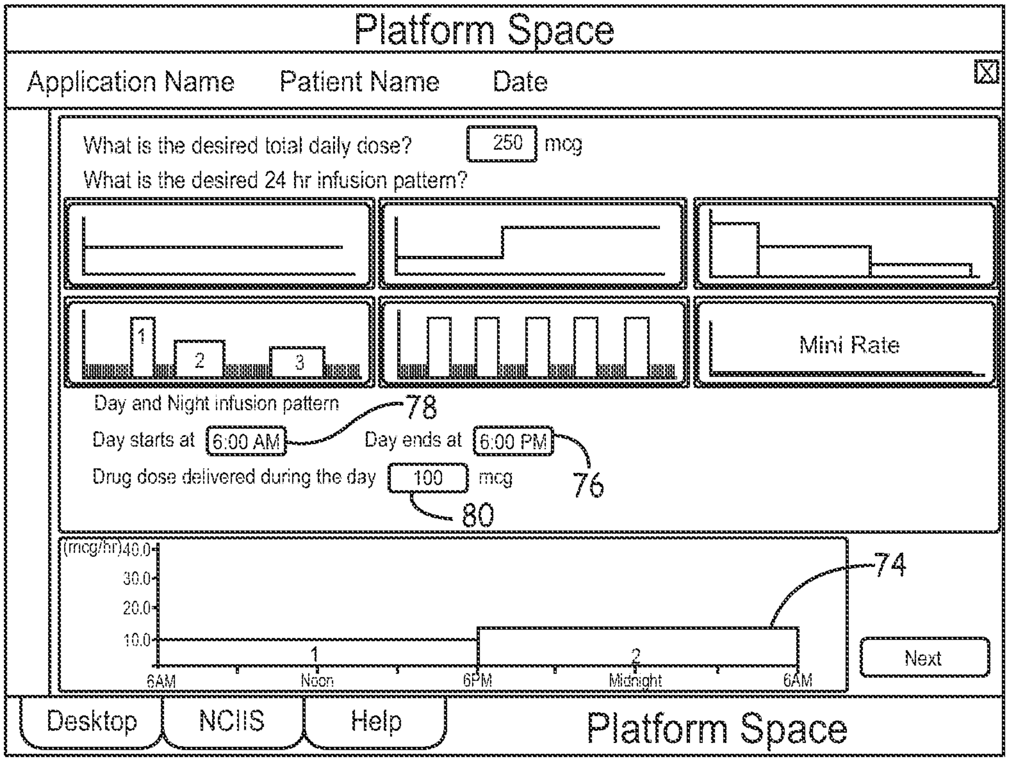
FIG. 35 is another screen shot showing the programming of a day and night infusion pattern.

FIG. 35 illustrates the entered day and night start time information 76, 78 as well as the drug dose to be delivered during the day 80. The graphical display 74 of the infusion program is now shown in solid form as enough information has been inputted by the user into the programmer 20 for the programmer 20 to consider the infusion program complete, or at least complete enough to show as solid and to control the therapy delivery. As may be appreciated, in various embodiments a different amount of information may be required for the programmer 20 to make the entered infusion program complete enough for controlling the drug infusion.

Figure 36:
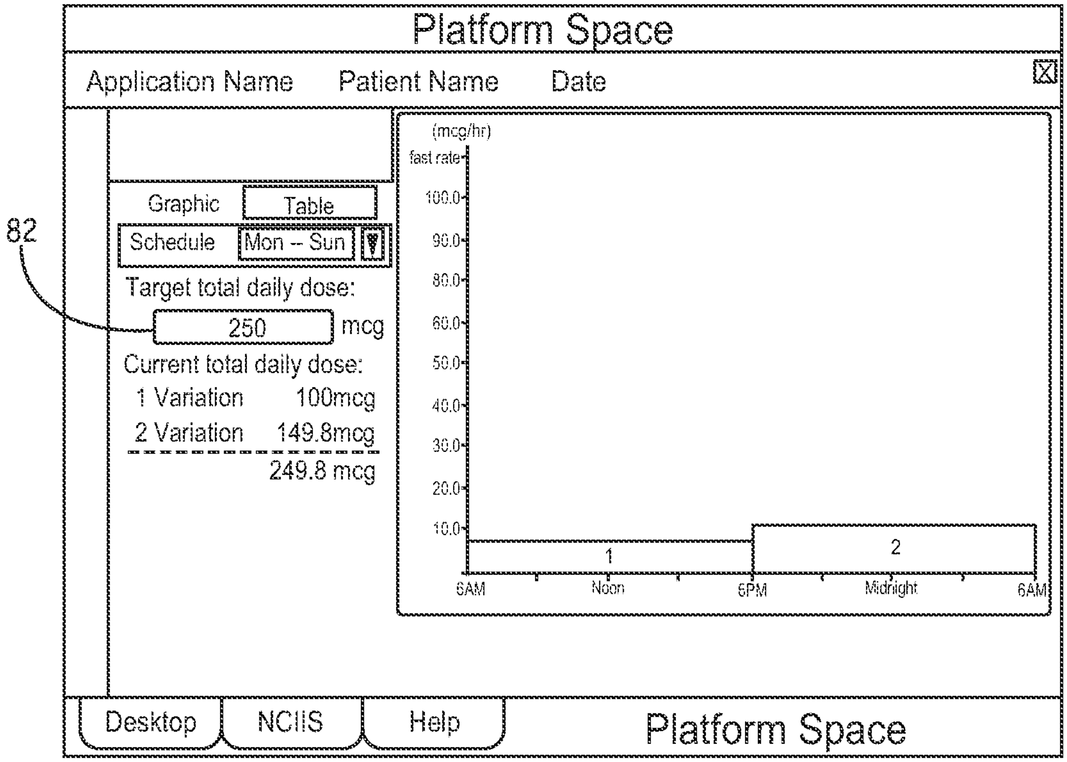
FIG. 36 is another screen shot showing the programming of a day and night infusion pattern.
Figure 37:
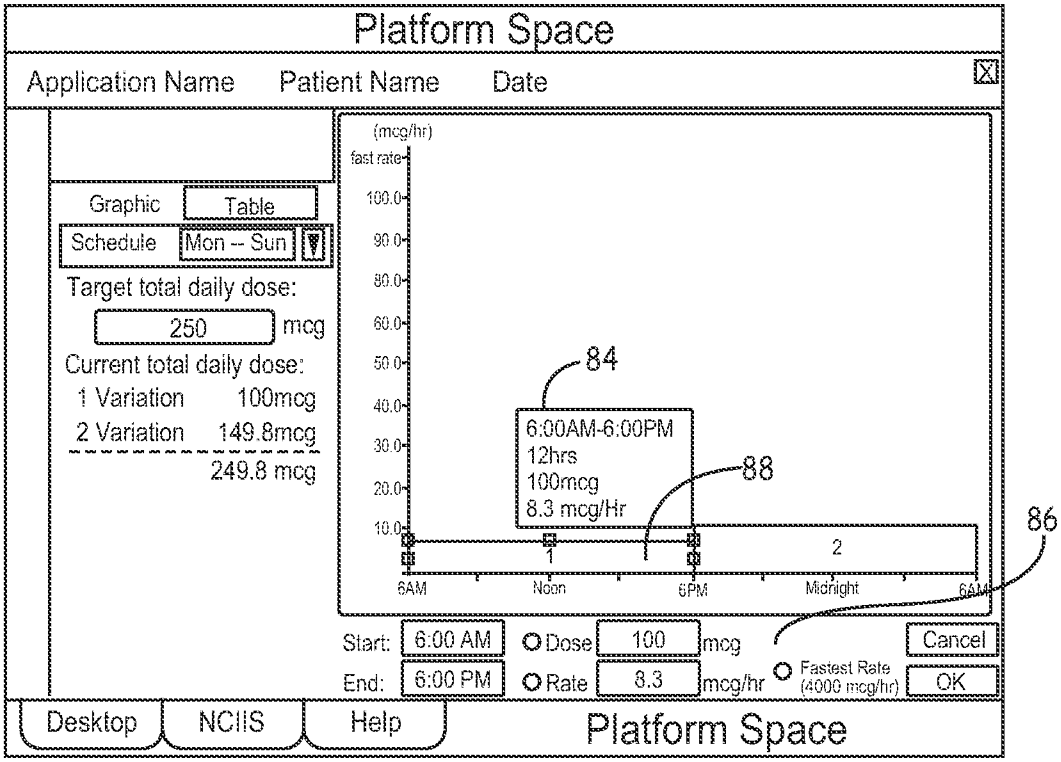
FIG. 37 is another screen shot showing the programming of a day and night infusion pattern.

FIG. 36 illustrates a screen shot in which the infusion program illustrated in FIG. 35 is shown in a different format. As illustrated, the total daily dosage is not exactly the amount previously given; the night dosage could only be adjusted to within 0.2 mcg of the total amount. Such approximations of the total daily dosage may be required due to pump limitations. In other instances the total dose for a period may not be easily divisible by the number of hours in that dosage cycle. The infusion program illustrated in FIG. 36 may be modified in any of the ways previously discussed. In addition, the target total daily dose may be adjusted in icon 82. FIG. 37 illustrates the user selecting the day portion of the day night infusion program. The specifics of the dosage are illustrated at 84 and icons at 86 illustrate various parameters that can be changed. The graphical display of the day dosage 88 can likewise be selected and modified by dragging portions of the box in a manner previously discussed. In addition, the information for the doses may be displayed graphically but the dosage information may be changed numerically using the illustrated icons for entering the information. In further embodiments additional windows may open up to enter the information for the dosage.

Figure 38:
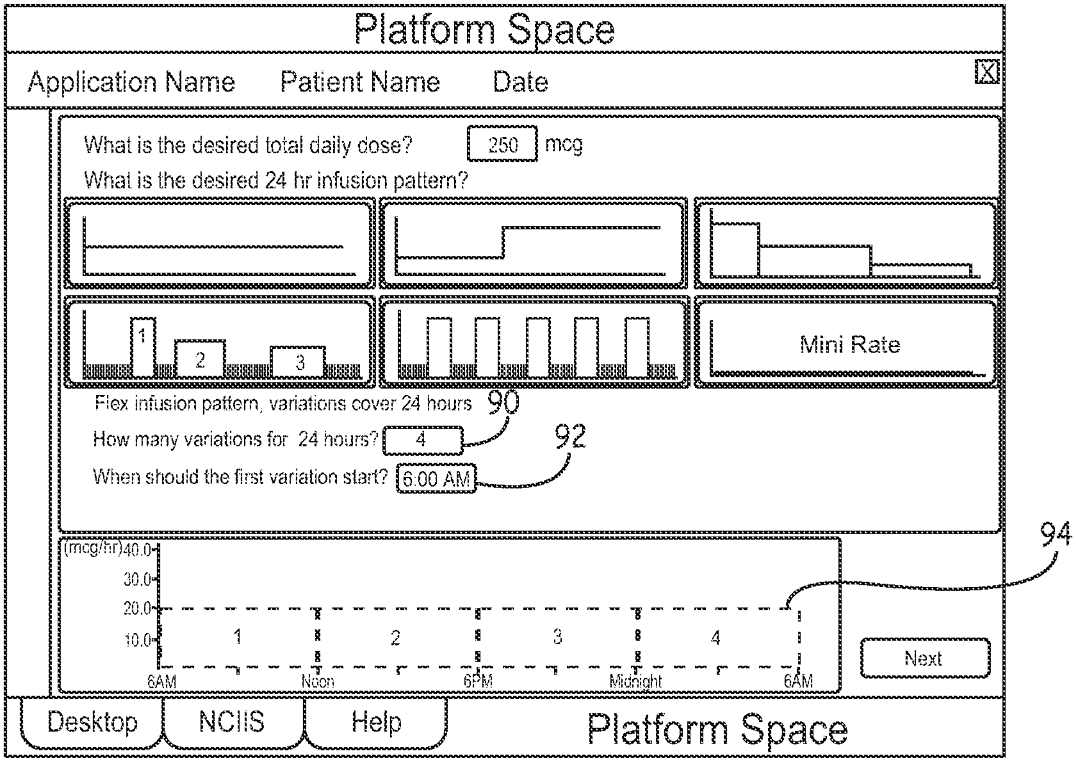
FIG. 38 is a screen shot showing the programming of a flex infusion pattern.

FIG. 38 illustrates an alternative dosage pattern selected from the screen illustrated in FIG. 32. In this case the dosage pattern is a flex infusion pattern, also known as a step pattern, with the number of steps entered at 90 and the timing of the first variation entered at 92. As previously discussed, the programmer 20 may first illustrate a tentative infusion program based on the limited information entered. In this embodiment the programmer 20 evenly divides a 24 hour day into four separate doses of equal size. In alternative embodiments more information may be entered before the graphical display of the tentative infusion program 92 is displayed, such as more start and stop times and dosage information. As may be appreciated, further screens may be also utilized to populate the required information to complete the infusion program. In addition, the infusion program 94 may be selected and modified by altering the shape of the dosage box by selecting using the pointing device and changing the shape of the dosage box in a manner previously discussed.

Various programming rules may be instituted to determine whether, when a box is expanded to a larger time, the other boxes are each proportionally shrunk or whether the immediately adjacent box is shrunk, or completely pinched out, during adjustment of the selected boxes. In one embodiment, growing (in duration) one step will shrink the immediately adjacent step. Likewise, shrinking (in duration) a step may grow the step immediately adjacent so as to avoid gaps between steps. Further rules may include a limitation on how short a step may be shrunk. For example, a minimum of 15 minutes may be established for each dosage period. In other embodiments a few seconds, a few minutes, such as 1, 5, or 10, or even multiples of hours may be the minimum dosage periods. The minimum limitation may be implemented for the dosage being actively manipulated and/or for the adjacent dosage that is being shrunk while the active dose is being expanded. Still further rules may be implemented in how high (or low) a box may be expanded (or shrunk). Height restrictions will insure that a dosage rate is not entered that is beyond the capability of the implantable device 14.

Figure 39:
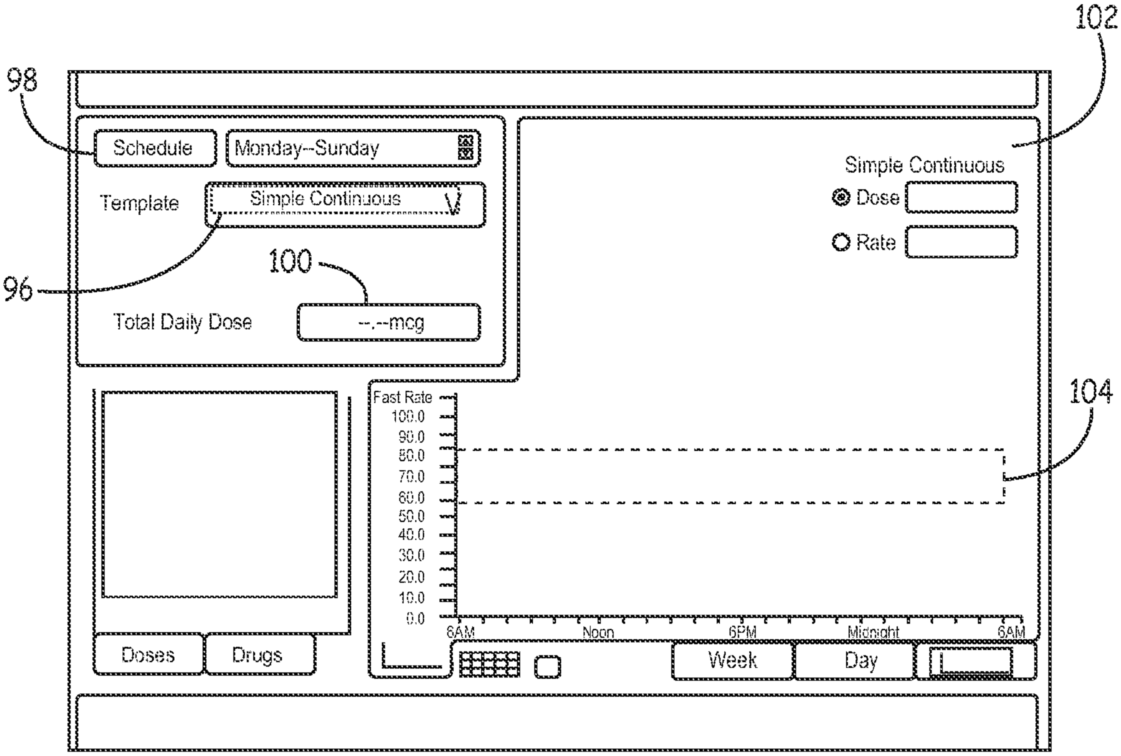
FIG. 39 is a screen shot showing an alternative embodiment screen for programming a simple continuous infusion pattern.
Figure 40:
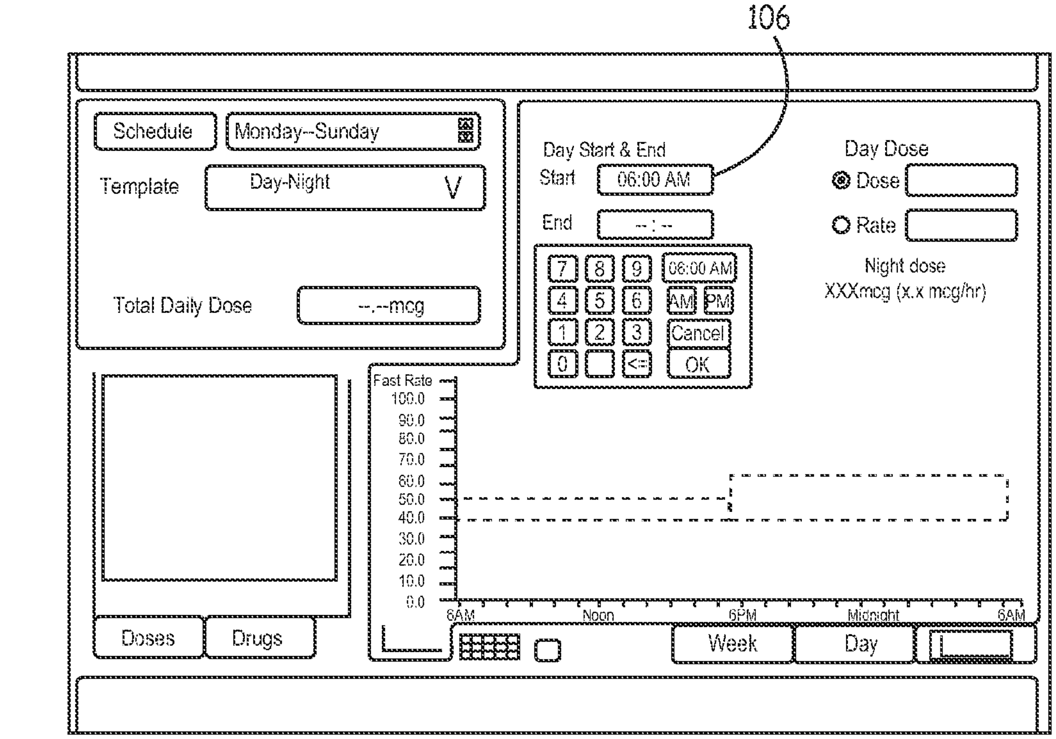
FIG. 40 is a screen shot showing an alternative embodiment screen for programming a day and night infusion pattern.

FIG. 39 is an alternative embodiment screen shot to FIG. 32 wherein the infusion pattern may be selected from a drop down menu 96. In addition, the total daily dose 100 may be entered and the days of the week to be programmed may also be entered 98. The user may also input the total dose or a desired rate 102. Once the required information is selected the programmer 20 may display a tentative dosing pattern 104. The dosing pattern 104 may not be anchored to the graph, or may float, because not enough information has been entered for the programmer 20 to make a solidified entry onto the display (the dosage pattern is in tentative format as previously discussed). Once enough information is entered the dosage may "drop" onto the correct position on the X and Y axis of the display and be available for editing. FIG. 40 illustrates another embodiment wherein a day and night program pattern has been selected. Further information icons may allow additional information to be input that is associated with the selected dosage pattern.

Figure 41:
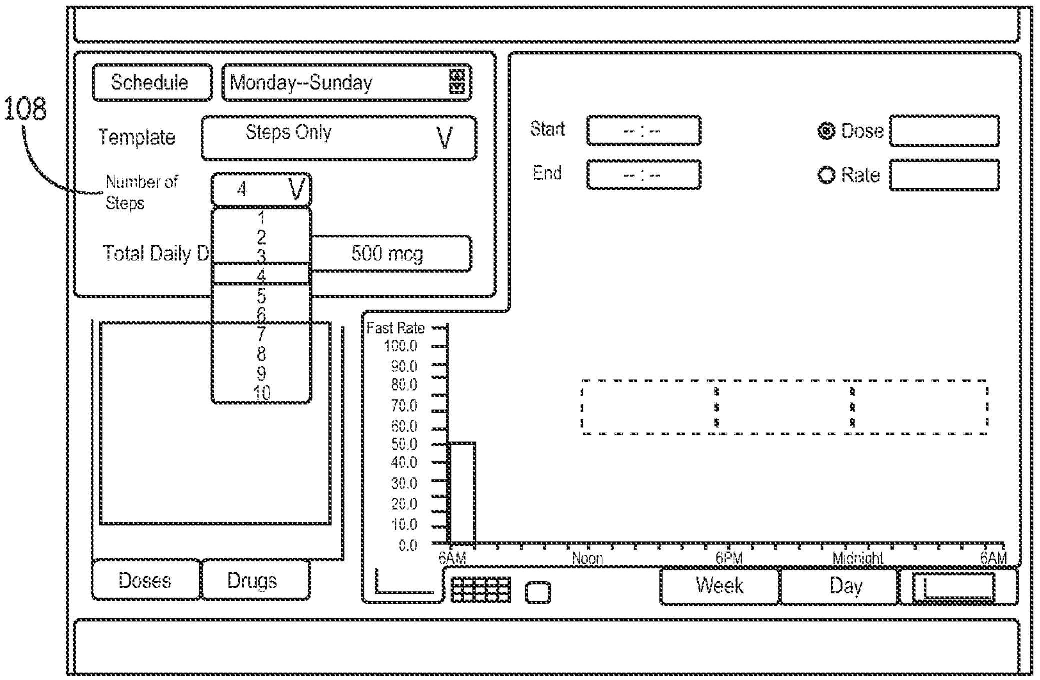
FIG. 41 is a screen shot showing an alternative embodiment screen for programming an infusion pattern with a set number of steps.
Figure 42:
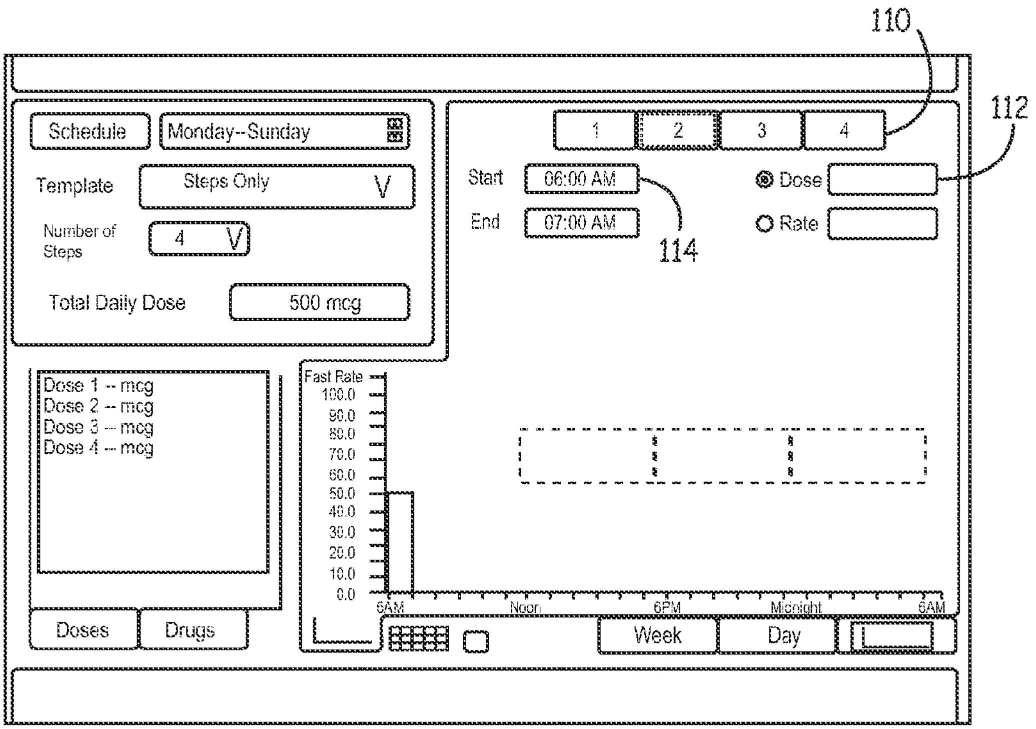
FIG. 42 is a screen shot showing the screen illustrated in FIG. 41 wherein one of the steps has been modified.

FIG. 41 illustrates another embodiment wherein an infusion pattern is entered. This infusion pattern is a steps, or flex, pattern. As illustrated, the programmer 20 may present the user with other icons that are associated with the selected dosage pattern, such as an icon for entering the desired number of steps 108. FIG. 42 illustrates the steps mode infusion pattern of FIG. 41 wherein 4 steps have been selected. An intermediate screen (not shown) may have illustrated each step in a tentative (dashed line) format. FIG. 42 illustrates a screen wherein the first step has been selected and modified with enough information to become a non-tentative step that is input into the program. Icons 110 may allow the user to select the step the user wishes to modify and icons 112, 114 may allow the user to enter parameters for the steps. In other embodiments the selection of the steps may be done in a variety of ways. Once the parameter for each dosage is entered the dosage pattern or infusion program may be complete.

Figure 43:
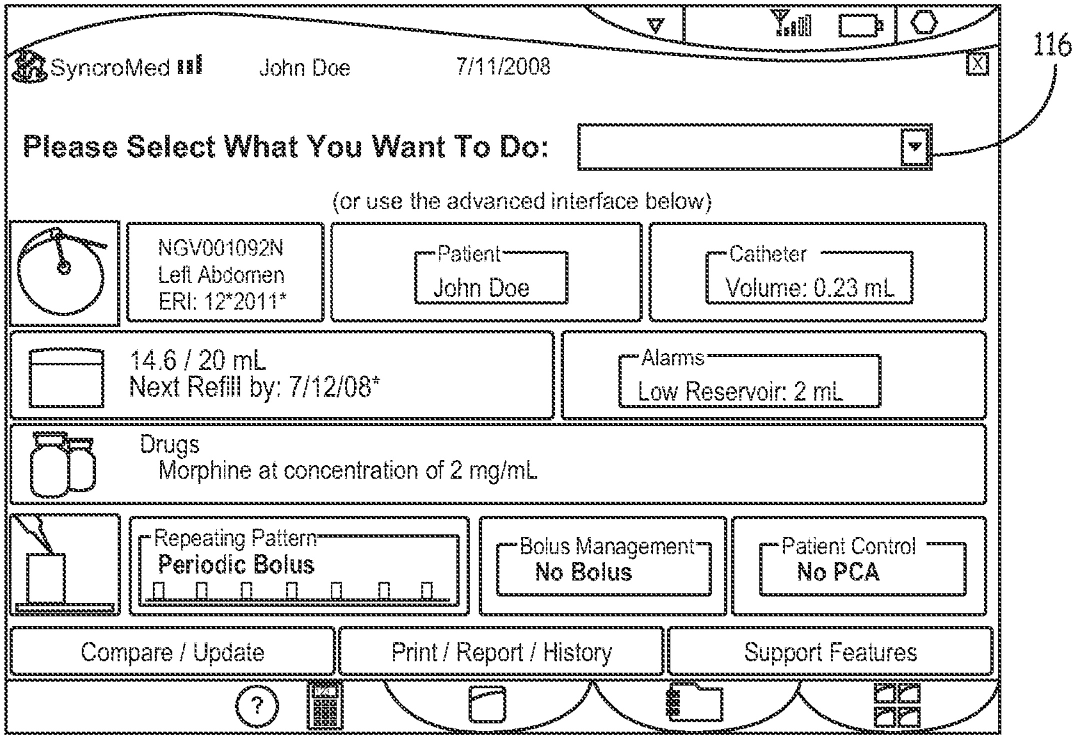
FIG. 43 is an alternative embodiment screen shot illustrating a screen for starting the programming session.

FIG. 43 illustrates an alternative embodiment navigation screen wherein the programmer 20 may display information about the patient and the relevant infusion device 14. In such an embodiment the user may select an action to undertake using the drop down menu 116 or may select one of the icons shown on the screen, labeled as the “advanced interface” menu. Such a screen may allow users to navigate through different options in a manner that is comfortable to that particular user.

Figure 44:
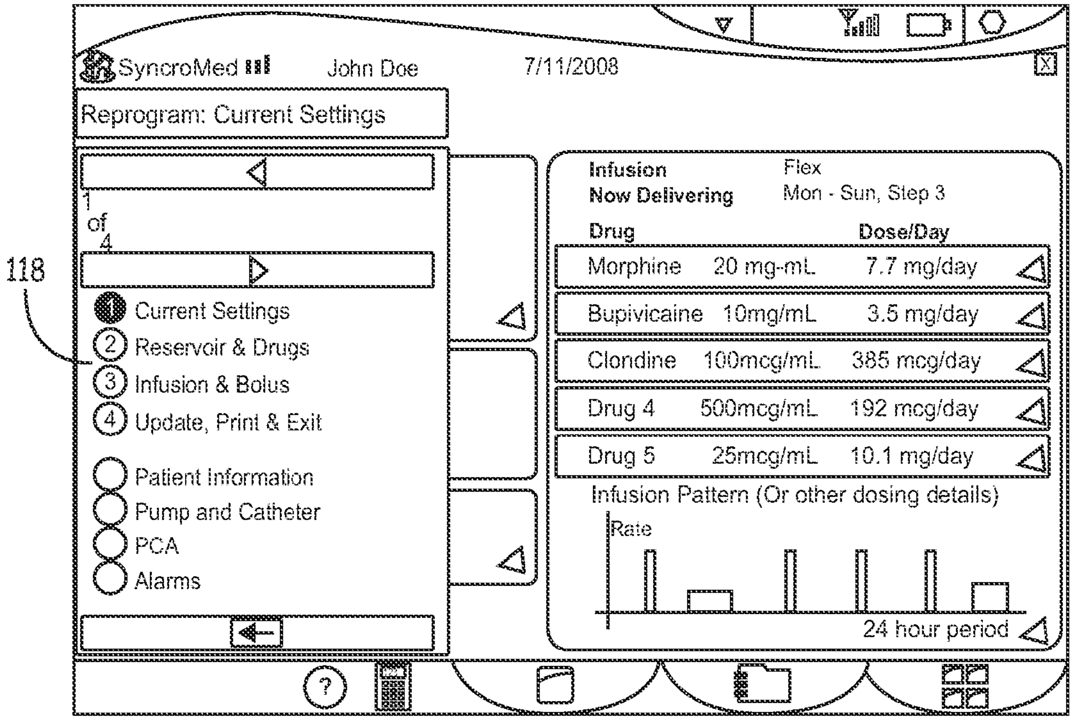
FIG. 44 is an alternative embodiment screen shot illustrating a method of navigating during a programming session.
Figure 45:
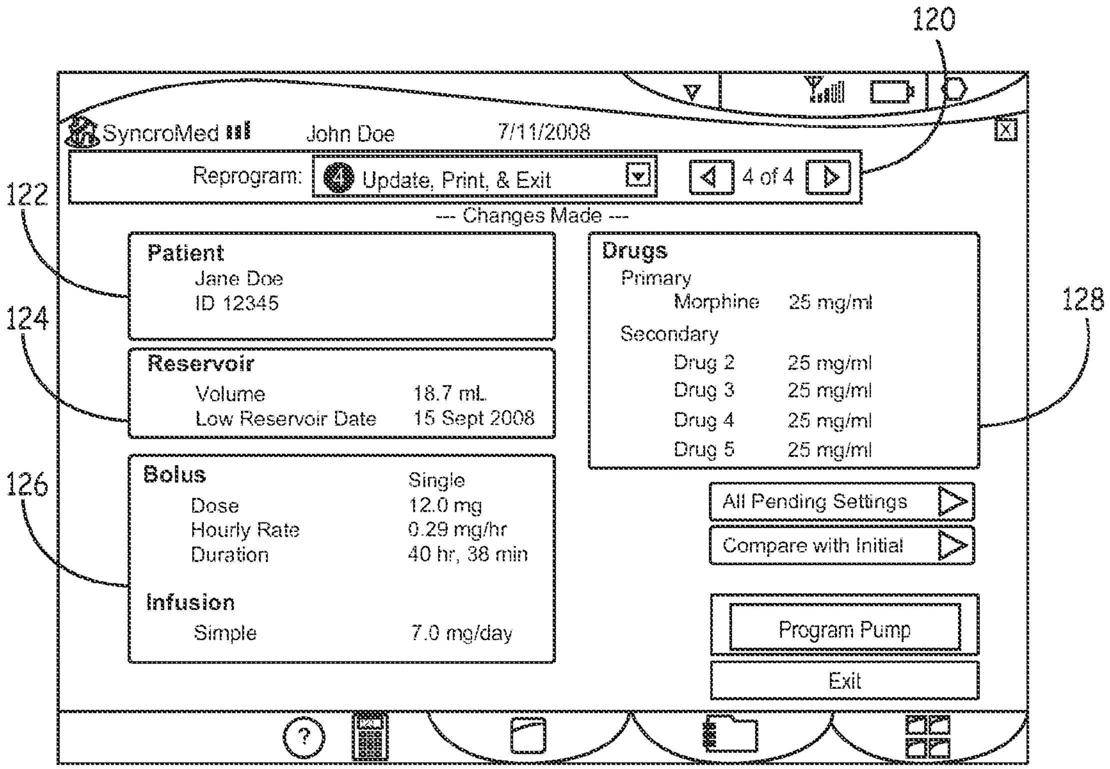
FIG. 45 is a screen shot showing an alternative embodiment screen for displaying patient information.
Figure 46:
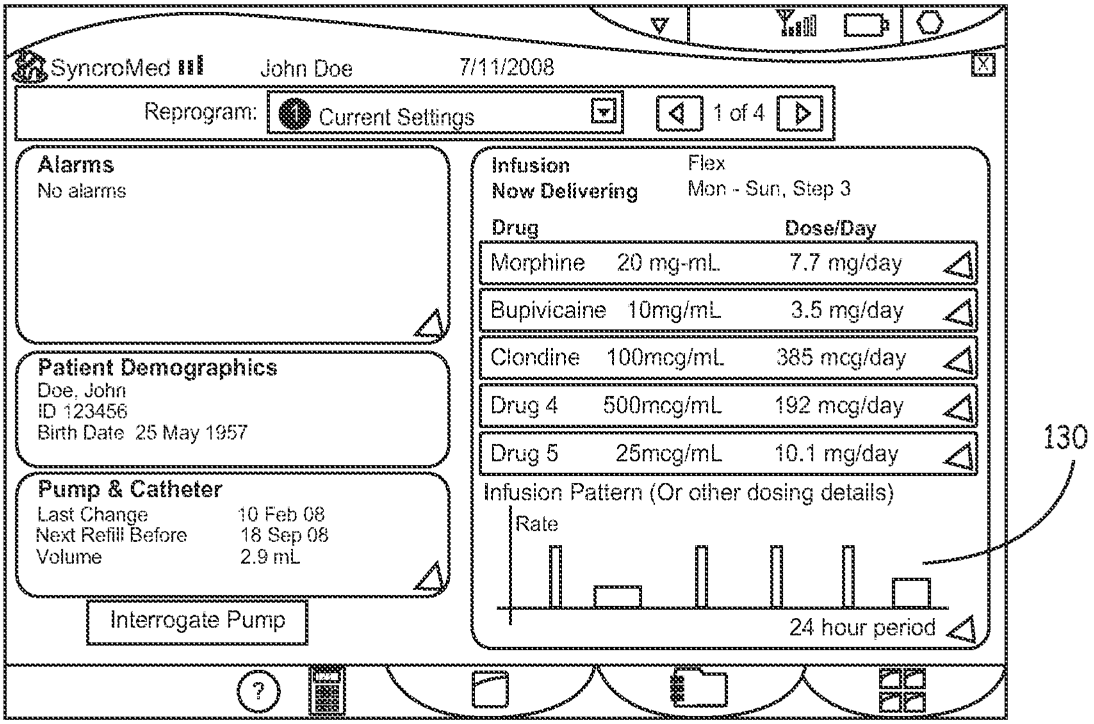
FIG. 46 is another screen shot showing an alternative embodiment screen for displaying patient information.

FIGS. 44-46 illustrate alternative embodiment screens for displaying patient specific information. Such screens may include a navigation pane 118 for moving between information screens and programming screens. The user may move through the selectable screens in a set order or may move around in any desired manner. FIG. 45 may an alternative navigation menu 120 and display similar information, including the patient information 122, reservoir size 124, infusion information 126, and drug infusion history 128. Each of the information boxes 122, 124, 126, 128 may have selectable tabs for modifying the information contained therein. FIG. 46 may include further information showing the infusion pattern or other dosing details 130.

While at least one exemplary embodiment has been presented in the foregoing detailed description of the invention, it should be appreciated that a vast number of variations exist. It should also be appreciated that the exemplary embodiment or exemplary embodiments are only examples and are not intended to limit the scope, applicability, or configuration of the invention in any way. Rather, the foregoing detailed description will provide those skilled in the art with a convenient road map for implementing exemplary embodiments of the invention, it being understood that various changes may be made in the function and arrangement of elements described in an exemplary embodiment without departing from the scope of the invention as set forth in the appended claims and their legal equivalents.

What is claimed is:

1. A method for programming a therapy delivery schedule of a medical device comprising:

receiving, via input drawn with a pointing device that engages a graphical user interface of a programmer of the medical device, one or more figures representing the desired therapy schedule, the one or more figures comprising multiple strokes, each of the multiple strokes being drawn by the pointing device being engaged with the graphical user interface; and translating, by the programmer, the figures that were received via input drawn with the pointing device into a therapy delivery schedule, wherein translating the figures comprises translating the multiple strokes, wherein at least one of the multiple strokes drawn by the pointing device within a screen of the graphical user interface is not connected to any other of the multiple strokes within the screen, and wherein receiving, via input drawn with a pointing device that engages the graphical user interface, one or more figures representing the desired therapy schedule, the one or more figures comprising multiple strokes further comprises receiving at least one of the multiple strokes that is spatially separated from the other strokes.

2. A method for programming a therapy delivery schedule of a medical device comprising:

receiving, via input drawn with a pointing device that engages a graphical user interface of a programmer of the medical device, one or more figures representing the desired therapy schedule, the one or more figures comprising multiple strokes, each of the multiple strokes being drawn by the pointing device being engaged with the graphical user interface; and translating, by the programmer, the figures that were received via input drawn with the pointing device into a therapy delivery schedule, wherein translating the figures comprises translating the multiple strokes, wherein at least one of the multiple strokes drawn by the pointing device within a screen of the graphical user interface is not connected to any other of the multiple strokes within the screen, and wherein receiving, via input drawn with a pointing device that engages the graphical user interface, one or more figures representing the desired therapy schedule, the one or more figures comprising multiple strokes further comprises receiving, via input drawn with one or more of a mouse, light pen, stylus, joystick, or trackball, one or more figures comprising multiple strokes.

3. A method for programming a therapy delivery schedule of a medical device comprising:

receiving, via input drawn with a pointing device that engages a graphical user interface of a programmer of the medical device, one or more figures representing the desired therapy schedule, the one or more figures comprising multiple strokes, each of the multiple strokes being drawn by the pointing device being engaged with the graphical user interface; and translating, by the programmer, the figures that were received via input drawn with the pointing device into a therapy delivery schedule, wherein translating the figures comprises translating the multiple strokes, and wherein at least one of the multiple strokes drawn by the pointing device within a screen of the graphical user interface is not connected to any other of the multiple strokes within the screen, and wherein receiving, via input drawn with a pointing device that engages the graphical user interface, one or more figures representing the desired therapy schedule, the one or more figures comprising multiple strokes further comprises receiving, via input drawn with a pointing device that engages a digitizing tablet, one or more figures.

4. A programmer for an implantable medical device comprising:

an interface configured to allow a user to graphically sketch one or more portions of an infusion program using a pointing device, the graphically sketched one or more portions comprising multiple strokes within a screen of the graphical user interface, at least one of the multiple strokes within the screen not being connected to any other of the multiple strokes within the screen, the sketched infusion program including at least one dosage amount scheduled to run over a desired time duration, both the dosage amount and the time duration created by the shape and location of the sketch; and a computer configured to interpret the sketch, and wherein the interface is configured to allow the pointing device to engage and disengage the interface for each of the strokes.

5. A method of creating an infusion program for a medical device using a controller, comprising:

presenting an interface that includes a graphical drawing tablet, wherein the graphical drawing tablet includes a screen comprising one axis for time and one axis for dosage rate;

receiving within the screen a pattern comprising multiple strokes drawn using a pointing device to indicate the desired dosage and time, at least one of the multiple strokes within the screen not being connected to any other of the multiple strokes within the screen; and analyzing, via the controller, the pattern comprising the multiple strokes drawn using a pointing device to obtain a therapy delivery schedule, wherein receiving the pattern comprises allowing the interface to be engaged and disengaged for each of the strokes.

6. A method for editing a therapy delivery schedule of a medical device comprising:

displaying, via a graphical user interface of a programmer for the medical device, one or more figures comprising strokes drawn with a pointing device on the graphical user interface, the figures representing the desired therapy schedule, each figure representing a therapy dosage;

receiving via the pointing device an edit drawn on one or more of the figures, whereby the edit comprises clicking and dragging to at least one of expand or contract one of the figures along a first axis to increase or decrease the duration of the therapy dosage represented by the figure and expand or contract one of the figures along a second axis to increase or decrease the rate of delivery of the therapy dosage represented by figure; and translating, via the programmer, the edit drawn via the pointing device to obtain a modified therapy delivery schedule.

7. The method of claim 6 wherein the graphical user interface comprises a touch screen.

8. The method of claim 6 wherein receiving via a pointing device an edit drawn on one or more of the figures further comprises expanding or contracting the figures with one or more of a mouse, light pen, stylus, joystick, or trackball.

9. A programmer for an implantable medical device capable of delivering therapeutic output to a patient comprising:

an interface through which one or more portions of an infusion program are entered by drawing with a pointing device on the interface and are graphically displayed via the interface as one or more figures, each figure graphically representing a dosage rate and a dosage duration by the size and shape of the figure; and a pointing device configured to edit one or more of the figures by clicking and dragging one of the figures along a first axis to increase or decrease one or more dosage durations or by clicking and dragging one of the figures along a second axis to increase or decrease one or more dosage rates, wherein the programmer is configured to translate the edits made to the one or more figures via the pointing device into changes to the infusion program.

10. The method of claim 1, wherein translating the figures that were drawn with a pointing device comprises using one of rectilinear patterns or a best-curve-fit feature.

11. A programmer for an implantable medical device comprising:

an interface configured to allow a user to graphically sketch one or more portions of an infusion program using a pointing device, the graphically sketched one or more portions comprising multiple strokes within a screen of the graphical user interface, at least one of the multiple strokes within the screen not being connected to any other of the multiple strokes within the screen, the sketched infusion program including at least one dosage amount scheduled to run over a desired time duration, both the dosage amount and the time duration created by the shape and location of the sketch; and a computer configured to interpret the sketch, wherein the computer is configured to interpret the sketch using one of rectilinear patterns or a best-curve-fit feature.

12. A programmer for an implantable medical device comprising:

an interface configured to allow a user to graphically sketch one or more portions of an infusion program using a pointing device, the graphically sketched one or more portions comprising multiple strokes within a screen of the graphical user interface, at least one of the multiple strokes within the screen not being connected to any other of the multiple strokes within the screen, the sketched infusion program including at least one dosage amount scheduled to run over a desired time duration, both the dosage amount and the time duration created by the shape and location of the sketch; and a computer configured to interpret the sketch, wherein the interface is configured to allow a user to modify via the pointing device a portion of the infusion program sketched using the pointing device, and wherein the computer is configured to interpret the modified portion.

13. The method of claim 5, wherein analyzing the pattern drawn using a pointing device to obtain a therapy delivery schedule comprises using one of rectilinear patterns or a best-curve-fit feature.

14. The method of claim 6, wherein translating the edit drawn via the pointing device to obtain a new therapy delivery schedule comprises using one of rectilinear patterns or a best-curve-fit feature.

15. The programmer of claim 9, wherein the programmer is configured to translate the edits made to the one or more figures via the pointing device using one of rectilinear patterns or a best-curve-fit feature.

16. The method of claim 1, wherein translating the figures that were received via input drawn with the pointing device comprises translating each of the multiple strokes into a separate dose before receiving another one of the multiple strokes.

17. The method of claim 1, wherein translating the figures that were received via input drawn with the pointing device comprises translating all of the multiple strokes after all of the multiple strokes are received.

18. A method for programming a therapy delivery schedule of a medical device comprising:

receiving, via input drawn with a pointing device that engages a graphical user interface of a programmer of the medical device, one or more figures representing the desired therapy schedule, the one or more figures comprising multiple strokes, each of the multiple strokes being drawn by the pointing device being engaged with the graphical user interface; and translating, by the programmer, the figures that were received via input drawn with the pointing device into a therapy delivery schedule, wherein translating the figures comprises translating the multiple strokes, wherein at least one of the multiple strokes drawn by the pointing device within a screen of the graphical user interface is not connected to any other of the multiple strokes within the screen, and wherein receiving, via input drawn with a pointing device that engages the graphical user interface, one or more figures representing the desired therapy schedule, the one or more figures comprising multiple strokes further comprises allowing the pointing device to engage and disengage the graphical user interface for each of the strokes.

19. The method of claim 1, wherein translating the figures comprises interpreting each of the strokes to create a respective infusion pattern.

20. The method of claim 1, wherein receiving, via input drawn with a pointing device that engages the graphical user interface, one or more figures representing the desired therapy schedule, the one or more figures comprising multiple strokes further comprises receiving imprecise marks and wherein translating the multiple figures comprises correcting or ignoring the imprecise marks.

21. A method for programming a therapy delivery schedule of a medical device comprising:

receiving, via input drawn with a pointing device that engages a graphical user interface of a programmer of the medical device, one or more figures representing the desired therapy schedule, the one or more figures comprising multiple strokes, each of the multiple strokes being drawn by the pointing device being engaged with the graphical user interface; and translating, by the programmer, the figures that were received via input drawn with the pointing device into a therapy delivery schedule, wherein translating the figures comprises translating the multiple strokes, wherein at least one of the multiple strokes drawn by the pointing device within a screen of the graphical user interface is not connected to any other of the multiple strokes within the screen, and wherein receiving, via input drawn with a pointing device that engages the graphical user interface, one or more figures representing the desired therapy schedule, the one or more figures comprising multiple strokes comprises receiving curves or slanted lines and wherein translating the multiple figures further comprises interpreting the curves or slanted lines as increasing or decreasing rates.

22. A programmer for an implantable medical device comprising:

an interface configured to allow a user to graphically sketch one or more portions of an infusion program using a pointing device, the graphically sketched one or more portions comprising multiple strokes within a screen of the graphical user interface, at least one of the multiple strokes within the screen not being connected to any other of the multiple strokes within the screen, the sketched infusion program including at least one dosage amount scheduled to run over a desired time duration, both the dosage amount and the time duration created by the shape and location of the sketch; and a computer configured to interpret the sketch, and wherein the computer is configured to translate each of the strokes to create a respective infusion pattern.

23. The programmer of claim 4, wherein each of the multiple strokes is spatially separated from others of the multiple strokes.

24. A programmer for an implantable medical device comprising:

an interface configured to allow a user to graphically sketch one or more portions of an infusion program using a pointing device, the graphically sketched one or more portions comprising multiple strokes within a screen of the graphical user interface, at least one of the multiple strokes within the screen not being connected to any other of the multiple strokes within the screen, the sketched infusion program including at least one dosage amount scheduled to run over a desired time duration, both the dosage amount and the time duration created by the shape and location of the sketch; and a computer configured to interpret the sketch, and wherein the interface is configured to allow imprecise marks to be received and wherein the computer is configured to correct or ignore the imprecise marks.

25. The programmer of claim 24, wherein the imprecise marks comprise overlapping strokes.

26. The programmer of claim 4, wherein the interface is configured to allow curves or slanted lines to be received and wherein the computer is configured to interpret the curves or slanted lines as increasing or decreasing rates.

27. The method of claim 5, wherein receiving the pattern comprises receiving a pattern comprising multiple disconnected strokes and analyzing the pattern comprises analyzing the multiple disconnected strokes.

28. The method of claim 5, wherein analyzing the pattern comprises interpreting each of the strokes to create a respective infusion pattern.

29. The method of claim 5, wherein receiving the pattern comprises receiving imprecise marks and wherein analyzing the pattern comprises correcting or ignoring the imprecise marks.

30. The method of claim 5, wherein receiving the pattern comprises receiving curves or slanted lines and wherein translating the pattern comprises interpreting the curves or slanted lines as increasing or decreasing rates.

31. A method for programming a therapy delivery schedule of a medical device comprising:

receiving, via input drawn with a pointing device that engages a graphical user interface of a programmer of the medical device, one or more figures representing the desired therapy schedule, the one or more figures comprising multiple strokes, each of the multiple strokes being drawn by the pointing device being engaged with the graphical user interface; and translating, by the programmer, the figures that were received via input drawn with the pointing device into a therapy delivery schedule, wherein translating the figures comprises translating the multiple strokes, wherein at least one of the multiple strokes drawn by the pointing device within a screen of the graphical user interface is not connected to any other of the multiple strokes within the screen, and wherein each of the multiple strokes comprises an electronic ink stroke.

32. A system, comprising:

a medical device;

an interface comprising a display screen;

a device configured to engage the interface to allow a user to draw multiple marks that are visible on the display screen at once, wherein at least one of the multiple marks is not connected to any other of the multiple marks that are visible on the display screen; and logic configured to translate the multiple marks within the display screen into a therapy delivery schedule for the medical device.

* * * * *